United States Patent [19]
Kleemann et al.

[11] Patent Number: 5,849,758
[45] Date of Patent: Dec. 15, 1998

[54] HERBICIDAL 2, 6-DISUBSTITUTED PYRIDINES AND 2, 4-DISUBSTITUTED PYRIMIDINES

[75] Inventors: Axel Kleemann, Gau-Alegesheim; Helmut Siegfried Baltruschat, Schweppenhausen; Thekla Hülsen, Amöneburg; Thomas Maier, Stockach; Stefan Scheiblich, Mainz, all of Germany

[73] Assignee: American Cyanamid Company, Madison, N.J.

[21] Appl. No.: 693,422

[22] Filed: Aug. 7, 1996

Related U.S. Application Data

[63] Continuation-in-part of Ser. No. 454,044, May 30, 1995, abandoned.

[51] Int. Cl.[6] .......................... A01N 43/54; C07D 239/02
[52] U.S. Cl. ........................................... 514/269; 544/319
[58] Field of Search .............................. 544/319; 514/269

[56] References Cited

U.S. PATENT DOCUMENTS

| | | | |
|---|---|---|---|
| 3,498,984 | 3/1970 | Santilli et al. | 260/256.5 |
| 3,940,395 | 2/1976 | Santilli et al. | 260/256.5 |
| 4,493,726 | 1/1985 | Burdeska et al. | 71/87 |

FOREIGN PATENT DOCUMENTS

WO 9607633  3/1996  WIPO .

*Primary Examiner*—Mukund J. Shah
*Assistant Examiner*—Tamthom T. Ngo
*Attorney, Agent, or Firm*—Gregory M. Hill, Esq.

[57] ABSTRACT

New herbicidal pyrimidine derivatives of general formula (I),

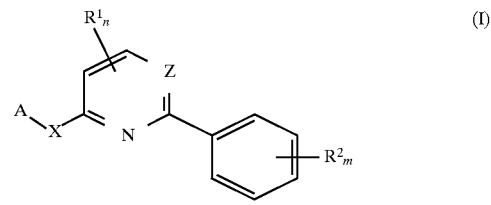

wherein Z represents a nitrogen atom; A represents a substituted aryl group or an optionally substituted pyridyl or pyrazolyl group; n represents an integer from 0 to 2 and $R^1$ or each $R^1$ independently represents a hydrogen atom or an optionally substituted alkyl, alkoxy, alkylthio or dialkylamino group; m represents an integer from 0 to 5 and $R^2$ or each $R^2$ independently represents a hydrogen or a halogen atom or an optionally substituted alkyl, haloalkyl, haloalkoxy, alkoxy, alkylthio group or a nitro, cyano or a halosulphonyl group; and X represents an oxygen or sulphur atom.

8 Claims, No Drawings

HERBICIDAL 2, 6-DISUBSTITUTED PYRIDINES AND 2, 4-DISUBSTITUTED PYRIMIDINES

This application is a continuation-in-part of U.S. application Ser. No. 8/454,044, filed May 30, 1995, now abandoned.

The present invention relates to certain 2,6-disubstituted pyridines and 2,4-disubstituted pyrimidines, their preparation and use as herbicides.

Pyridines, pyrimidines and their derivatives have many uses in the pharmaceutical area as well as in agriculture (herbicides, fungicides, acaricides, anthelmintics, bird repellents), reagents, intermediates and chemicals for the polymer and textile industry.

2-Arylpyrimidines and 2-pyrimidinyl-6-arylpyridines for example have been described as fungicides (DE 40 29 654 and JO 2131-480, respectively). EP 263,958 is concerned with herbicidal 2,6-diphenylpyridines, and structurally related 2,4-diphenylpyrimidines have been disclosed in EP 354,766 and 425,247, respectively, which are also said to be herbicides. Another example are 2,6-diphenoxypyridines, which have been published in EP 572,093 as herbicides. 4-Phenoxy-2-pyrazol-1-yl-pyrimidines are disclosed in DE 29 35 578 to have fungicidal activity. Huelsen (Diplomarbeit, Konstanz 1993) describes four distinct 2-(1-methyl-3-trifluoromethylpyrazol-5-yloxy)-6-phenyl pyridines, however, no biological activity is disclosed.

Surprisingly, it has now been found that good herbicidal activity is present in novel pyridine and pyrimidine derivatives having both an aryl group and an aryloxy or a heteroaryloxy group. These compounds unexpectedly show excellent activity and good crop selectivity in pre- and post-emergence applications on both broadleaf and grassy weed species. Accordingly, the present invention provides 2,6-substituted pyridines and 2,4-substituted pyrimidines of the general formula I

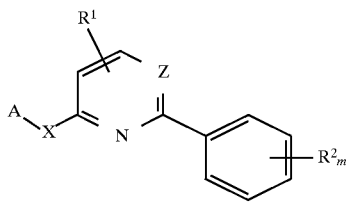

wherein
A represents an optionally substituted aryl group or an optionally substituted 5- or 6-membered nitrogen-containing heteroaromatic group or a difluorobenzodioxolyl group;
m represents an integer from 0 to 5;
n represents an integer from 0 to 2;
$R^1$ (or each $R^1$) independently represents a hydrogen atom, a halogen atom, an optionally substituted alkyl, alkenyl, alkynyl, alkoxy, alkoxyalkyl, dialkoxyalkyl, alkoxyalkoxy, alkylthio, amino, alkylamino, dialkylamino, alkoxyamino or formamidino group;
$R^2$ (or each $R^2$) independently represents a hydrogen atom, a halogen atom, an optionally substituted alkyl, alkenyl, alkynyl, haloalkyl, haloalkoxy, alkoxy, alkoxyalkyl, alkoxyalkoxy, alkylthio, haloalkylthio group or a nitro, cyano, $SF_5$ or a alkylsulphonyl or alkylsulfinyl group;
X represents an oxygen or sulphur atom; and
Z represents a nitrogen atom or a CH group;

with the proviso that if A represents a 1-methyl-3-trifluoromethyl-pyrazol-5-yl group, n is 0, X represents an oxygen atom and Z represents a CH group, then $R^2_m$ does not represent hydrogen or 3-trifluoromethyl or 2,4-dichloro or 2,4-dimethyl.

An aryl group as substituent or part of other substituents or in the definition of A is suitably an optionally substituted phenyl or naphthyl group. Within the definition of A the 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. As far as A is concerned the definition "aryl" does also include bicyclic systems which consist of a benzene ring condensed with a 5- or 6-membered heterocyclic ring as defined above and in turn the 5- or 6-membered heterocycles may be condensed with a benzene ring. Another preferred embodiment of A is a difluorobenzodioxolyl group of formula

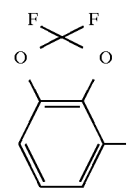

Generally, if any of the above mentioned moieties comprises an alkyl, alkenyl or alkynyl group, such groups, unless otherwise specified, may be linear or branched and may contain 1 to 12, preferably 1 to 4, carbon atoms. Examples of such groups are methyl, ethyl, propyl, vinyl, allyl, isopropyl, butyl, isobutyl and tertiary-butyl groups. The alkyl portion of a haloalkyl, haloalkoxy, alkylthio, haloalkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl, haloalkylthio and haloalkoxy are preferably mono-, di- or trifluoroalkyl, alkylthio and alkoxy, especially trifluoromethyl, difluoromethoxy, trifluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$alkoxy, $C_{1-4}$haloalkoxy and $C_{1-4}$alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxyl, $C_{1-4}$alkyl, $C_{1-4}$alkoxy, $C_{1-4}$haloalkyl, $C_{1-4}$haloalkoxy, $C_{1-4}$haloalkylthio and halosulfanyl groups such as $SF_5$. 1 to 5 substituents may suitably be employed, 1 to 2 substituents being preferred. Typically haloalkyl, haloalkoxy and haloalkylthio groups are trifluoromethyl, trifluoromethoxy, difluoromethoxy and trifluoromethylthio groups.

The index m preferably means an integer from 1 to 3, n is preferably 1 (then $R^1$ is not hydrogen).

The compounds according to general formula I are oils, gums, or, predominantly, crystalline solid materials. They can be used in agriculture or related fields for the control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application. The compounds of general formula I according to the invention possess a high herbicidal activity within a wide concentration range and may be used in agriculture.

Preferred compounds are those wherein A represents a phenyl, pyridyl, or pyrazolyl group, being substituted by one or more identical or different substituents selected from halogen atoms, alkyl, alkoxy, haloalkyl, haloalkoxy and pentahalosulfanyl groups.

Especially preferred are compounds bearing a substituent in group A in meta-position relative to the point of attachment of this group.

Good results in terms of control of undesired plant growth are obtained when A is meta-substituted by a chlorine atom or a trifluoromethyl group, especially A being a 2-chloropyrid-4-yl, 1-methyl-3-trifluoromethyl-pyrazol-5-yl or 3-trifluoromethylphenyl group.

Particularly good results in control of weeds are achieved with compounds wherein X represents an oxygen atom. Especially good results are obtained with compounds wherein Z represents a nitrogen atom.

The following formula Ia represents a preferred embodiment of the invention:

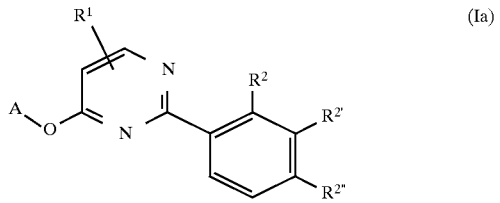

(Ia)

In this formula A represents 3-trifluoromethyl-phenyl, 2-chloropyrid-4-yl, 2-trifluoromethylpyrid-4-yl, 2-difluoromethoxypyrid-4-yl or 1-methyl-3-trifluoromethylpyrazol-5-yl, $R^1$ has the meaning given above; $R^2_1$, $R^{2'}$ and $R^{2''}$ independently represent a hydrogen atom, a fluorine, chlorine or bromine atom, one or two of them also a trifluoromethyl, trifluormethoxy or a cyano group, $R^{2''}$ can further be a $C_1$–$C_4$alkyl group, particularly tert-butyl.

The invention is exemplified by the following compounds:

2-(1'-methyl-3'-trifluoromethylpyrazol-5'-yloxy)-6-(4''-trifluoromethylphenyl)pyridine,
2-(2',4'-difluorophenyl)-6-methyl-4-(1''-methyl-3''-trifluoromethylpyrazol-5''-yloxy)pyrimidine,
2-(2',4'-difluorophenyl)-6-methyl-4-(3''-trifluoromethylphenoxy)pyrimidine,
2-(2'-chloropyrid-4'-yloxy)-(4''-trifluoromethylphenyl)-pyridine,
2-(2'-chloropyrid-4'-yloxy)-6-(3''-trifluoromethylphenyl)-pyridine,
2-(3'-chlorophenyl)-5-methyl-4-(1''-methyl-3''-trifluoromethylpyrazol-5''-yloxy)pyrimidine,
2-(3'-chlorophenyl)-5-methyl-4-(3''-trifluoromethylphenoxy)pyrimidine,
2-(4'-fluorophenyl)-6-methyl-4-(3''-trifluoromethylphenoxy) pyrimidine,
2-(4'-fluorophenyl)-4-(1''-methyl-3''-trifluoromethyl-pyrazol-5''-yloxy)-5-methylpyrimidine,
2-(4'-fluorophenyl)-4-(1''-methyl-3''-trifluoromethyl-pyrazol-5''-yloxy)-6-methyl-pyrimidine,
4-(2''-chloropyrid-4''-yloxy)-2-(2',4'-difluorophenyl)-5-methylpyrimidine,
4-(2''-chloropyrid-4''-yloxy)-5,6-dimethyl-2-(4'-trifluoromethoxyphenyl)pyrimidine,
4-(2''-chloropyrid-4''-yloxy)-5,6-dimethyl-2-(4'-trifluoromethylphenyl)pyrimidine,
4-(2''-chloropyrid-4''-yloxy)-5-methyl-2-(4'-trifluoromethoxyphenyl)pyrimidine,
4-(2''-chloropyrid-4''-yloxy)-5-methyl-2-(4'-trifluoromethylphenyl)pyrimidine,
4-(2''-chloropyrid-4''-yloxy)-6-methyl-2-(4'-trifluoromethoxyphenyl)pyrimidine,
4-(2''-chloropyrid-4''-yloxy)-6-methyl-2-(4'-trifluoromethylphenyl)pyrimidine,
5-ethyl-6-(4''-trifluoromethylphenyl)-2-(3'-trifluoromethylphenoxy)pyridine,
4-methyl-6-(4''-trifluoromethoxyphenyl)-2-(1'-methyl-3'-trifluoromethylpyrazol-5'-yloxy)pyridine,
4-methyl-6-(4''-trifluoromethoxyphenyl)-2-(2'-chloropyrid-4'-yloxy)pyridine,
4-methyl-6-(4''-trifluoromethylphenyl)-2-(1'-methyl-3'-trifluoromethylpyrazol-5'-yloxy)pyridine,
4-methyl-6-(4''-trifluoromethylphenyl)-2-(2'-chloropyrid-4'-yloxy)pyridine,
4-methyl-6-(4''-fluorophenyl)-2-(1'-methyl-3'-trifluoromethylpyrazol-5'-yloxy)pyridine,
5,6-dimethyl-2-(4'-trifluoromethoxyphenyl)-4-(1''-methyl-3''-trifluoromethylpyrazol-5''-yloxy)pyrimidine,
5,6-dimethyl-2-(4'-trifluoromethoxyphenyl)-4-(3''-trifluoromethylphenoxy)pyrimidine,
5,6-dimethyl-2-(4'-trifluoromethylphenyl)-4-(3''-trifluoromethylphenoxy)pyrimidine,
5,6-dimethyl-4-(1''-methyl-3''-trifluoromethylpyrazol-5''-yloxy)-2-(4'-trifluoromethylphenyl)pyrimidine,
5-methyl-2-(3'-methylphenyl)-4-(1''-methyl-3''-trifluoromethylpyrazol-5''-yloxy)pyrimidine,
5-methyl-2-(3'-methylphenyl)-4-(3''-trifluoromethylphenoxy)pyrimidine,
5-methyl-2-(4'-trifluoromethoxyphenyl)-4-(1''-methyl-3''-trifluoromethylpyrazol-5''-yloxy)pyrimidine,
5-methyl-2-(4'-trifluoromethoxyphenyl)-4-(3''-trifluoromethylphenoxy)pyrimidine,
5-methyl-2-(4'-trifluoromethylphenyl)-4-(1''-methyl-3''-trifluoromethylpyrazol-5''-yloxy)pyrimidine,
5-methyl-4-(3''-trifluoromethylphenoxy)-2-(4'-trifluoromethylphenyl)pyrimidine,
6-(4''-fluorophenyl)-2-(1'-methyl-3'-trifluoromethylpyrazol-5'-yloxy)pyridine,
6-methyl-2-(4'-trifluoromethoxyphenyl)-4-(1''-methyl-3''-trifluoromethylpyrazol-5''-yloxy)pyrimidine
6-methyl-2-(4'-trifluoromethoxyphenyl)-4-(3''-trifluoromethylphenoxy)pyrimidine,
6-methyl-4-(3''-trifluoromethylphenoxy)-2-(4'-trifluoromethylphenyl)pyrimidine, 6-methyl-2-(4'-trifluoromethylphenyl)-4-(1"-methyl-3"-pentafluoroethylpyrazol-5"-yloxy)pyrimidine 6-methyl-2-(4'-cyanophenyl)-4-(1"-methyl-3"-pentafluoroethylpyrazol-5"-yloxy)pyrimidine 6-methoxy-2-(4'-cyanophenyl)-4-(1"-methyl-3"-pentafluoroethylpyrazol-5"-yloxy)pyrimidine 6-methyl-4-(2",2"-difluoro-1",3"-benzodioxol-4"-yloxy)-2-(4'-trifluoromethylphenyl)pyrimidine 6-ethyl-2-(4'-trifluoromethylphenyl)-4-(1"-methyl-3"-trifluoromethylpyrazol-5"-yloxy)pyrimidine 6-ethyl-2-(4'-trifluoromethylphenyl)-4-(3"-trifluoromethylphenoxy)pyrimidine 6-methyl-2-(4'-methylsulfonylphenyl)-4-(1"-methyl-3"-pentafluoroethylpyrazol-5"-yloxy)pyrimidine 6-ethyl-2-(4'-trifluoromethylphenyl)-4-(2'-chloropyrid-4'-yloxy)pyrimidine 6-propargyl-2-(4'-trifluoromethylphenyl)-4-(1"-methyl-3"-trifluoromethylpyrazol-5"-yloxy)pyrimidine 6-methoxymethyl-2-(4'-chlorophenyl)-4-(1"-methyl-3"-trifluoromethylpyrazol-5"-yloxy)pyrimidine 6-methoxymethyl-2-(4'-chlorophenyl)-4-(3"-trifluoromethylphenoxy)pyrimidine 4-(3"-trifluoromethylphenoxy)-2-(4'-trifluoromethylphenyl)pyrimidine 4-(1"-methyl-3"-trifluoromethylpyrazol-5"-yloxy)-2-(4'-trifluoromethylphenyl)pyrimidine 6-chloro-2-(4'-trifluoromethylphenyl)-4-(1"-methyl-3"-trifluoromethylpyrazol-5"-yloxy)pyrimidine 6-bromo-2-(4'-trifluoromethylphenyl)-4-(1"-methyl-3"-trifluoromethylpyrazol-5"-yloxy)pyrimidine 6-chloro-2-(4'-chloromethylphenyl)-4-(1"-methyl-3"-trifluoromethylpyrazol-5"-yloxy)pyrimidine 6-fluoro-2-(4'-trifluoromethylphenyl)-4-(1"-methyl-3"-trifluoromethylpyrazol-5"-yloxy)pyrimidine 6-methoxy-2-(4'-trifluoromethylphenyl)-4-(3"-trifluoromethylphenoxy)pyrimidine, 6-methoxy-2-(4'-trifluoromethylphenyl)-4-(1"-methyl-3"-trifluoromethylpyrazol-5"-yloxy)pyrimidine 6-methoxy-2-(4'-trifluoromethylphenyl)-4-(2'-chloropyrid-4'-yloxy)pyrimidine, 5-methoxy-2-(4'-trifluoromethylphenyl)-4-(3"-trifluoromethylphenoxy)pyrimidine, 5-methoxy-2-(4'-trifluoromethylphenyl)-4-(1"-methyl-3"-trifluoromethylpyrazol-5"-yloxy)pyrimidine 5-methoxy-2-(4'-trifluoromethylphenyl)-4-(2'-chloropyrid-4'-yloxy)pyrimidine, 6-ethylamino-2-(4'-trifluoromethylphenyl)-4-(1"-methyl-3"-trifluoromethylpyrazol-5"-yloxy)pyrimidine 6-methoxyamino-2-(4'-chlorophenyl)-4-(1"-methyl-3"-trifluoromethylpyrazol-5"-yloxy)pyrimidine 6-vinyl-2-(4'-trifluoromethylphenyl)-4-(1"-methyl-3"-trifluoromethylpyrazol-5"-yloxy)pyrimidine The compounds according to the invention can be prepared by conventional methods.

A suitable process for the preparation of the compounds of general formula I comprises the reaction of a compound of general formula III

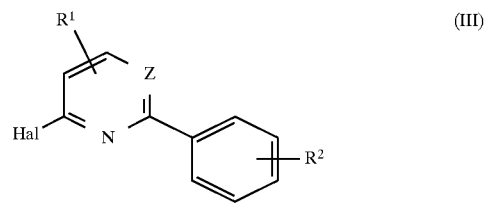

with a compound of general formula IV

A—XM  (IV)

wherein Z, A, $R^1$, $R^2$, m, n and X are as defined hereinbefore; Hal represents a halogen atom; and M represents a metal atom.

The halogen atom Hal may be any halogen atom, suitably a fluorine, chlorine or bromine atom. The metal atom M may be any metal atom, suitably alkali metal atoms. Sodium and potassium being preferred.

Alternatively, a compound of general formula XV

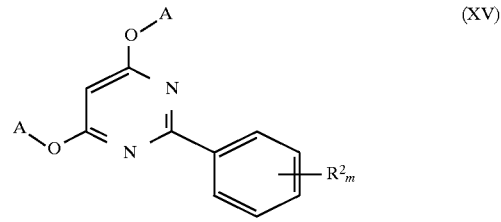

wherein A, $R^2$ and m are as defined hereinbefore, may react with $R^1$—H, preferable in the presence of a base, if $R^1$ is optionally substituted alkoxy, alkoxyalkoxy, alkylthio, amino, alkylamino, dialkylamino or alkoxyamino to give compound of general formula I.

Compounds I, wherein $R^1$ is alkynyl or alkenyl, e.g. of the allyl or propargyl types, can be prepared from compounds I, wherein $R^1$ is a halogen atom, preferably chlorine or bromine, by reaction of $R^1$—H or organometal derivatives thereof, preferable in the presence of a transition metal catalyst or a base.

Compounds XV can be prepared from III, wherein $R^1$ is Hal, Z is nitrogen, Hal, $R^2$ and m are defined as hereinbefore, by reaction with IV as described above, X means oxygen, applying about 2 equivalents of IV.

In practice, the reaction may be carried out in the absence or presence of a solvent which promotes the reaction or at least does not interfere with it. Preferred are polar, aprotic or protic solvents, suitably being N,N-dimethylformamide or dimethylsulfoxide or sulfolane, or an ether, such as tetrahydrofuran or dioxane, or alcohols, or water or mixtures thereof. The reaction is carried out at a temperature between ambient temperature and the reflux temperature of the reaction mixture, preferably at elevated temperature, especially reflux temperature.

Compounds of formula III in which Z represents a C—H group and n is 0 may be obtained by reacting a compound of general formula V

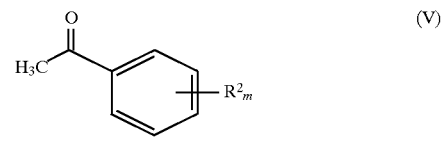

wherein $R^2$ and m are as defined hereinbefore, with an aldehyde, suitably formaldehyde, and a dialkylamine, suitably dimethylamine, according to *Org. Synthesis* Col. Vol.

III, 305f, in a solvent, conveniently an alcohol, preferably ethanol, to give a compound of general formula VI,

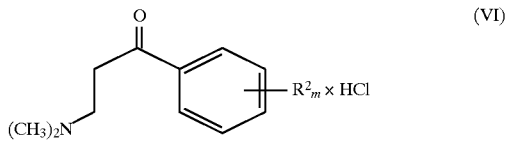

which is subsequently reacted according to DBP 21 47 288 (1971) with an ammonium salt, suitably ammonium acetate, and a compound of general formula VII,

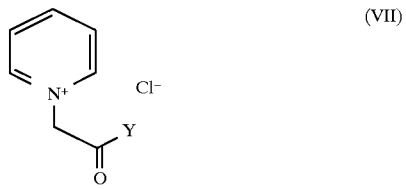

wherein Y is an alkoxy group or an $NH_2$-group, preferably an ethoxy group, in a solvent, suitably an alcohol, preferably ethanol, to give a compound of general formula VIII,

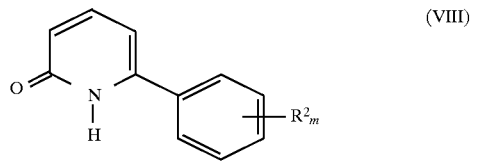

which is further converted by reacting VIII with phosphoryl halogenides (Müller, E., *Chem. Ber.* 42, 423 (1909); Katritzky et al., *J. Chem. Soc., Perkin Trans.* Part 1, 1980, 2743–2754), preferably phosphoryl bromide or phosphoryl chloride at elevated temperatures, ideally reflux temperature, to give a compound of general formula III.

An alternative, and preferred process for the preparation of compounds of general formula III in which Z represents a C—H group, comprises reacting a 2,6-dihalopyridine of general formula IX

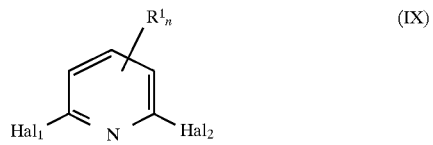

wherein $R^1$ and n are as defined hereinbefore, and each $Hal_1$ and $Hal_2$ independently represents a halogen atom, with an organometallic benzene derivative of general formula (X) in an approximately equimolar ratio,

wherein $R^2$ and m are defined as hereinbefore, and M represents an alkali metal atom, or borine, or tin, or magnesium, or zinc or copper optionally in the presence of a transition metal catalyst.

The alkali metal may be any alkali metal, preferably lithium, and the reaction may be carried out in an aprotic, polar solvent, preferably ethers, to give a compound of general formula III, essentially as disclosed in Cook and Wakefield, *J. Chem. Soc.*, 1969, 2376, or in unpolar solvents or water, for example as described in Ali, N. M. et al, *Tetrahedron*, 1992, 8117.

Compounds of formula III, where Z means CH, Hal is fluorine, $R^1$ is hydrogen, $R^2$ and m are as defined hereinbefore, can further be converted to compounds of formula III, where n=1, Z means CH, Hal is fluorine, $R^2$, m are as defined hereinbefore and $R^1$ is in position 3 and means methylthio (or another group from the set described before, that is introducable in form of an electrophilic reagent), analogous to the method described by Gungor, T, Marsais, F. and Queguiner, G, *J. Organometallic Chem.*, 1981, 139–150.

A process for the preparation of compounds of formula III, in which Z represents a nitrogen atom, comprises the reaction of benzamidine hydrochlorides of the general formula XI

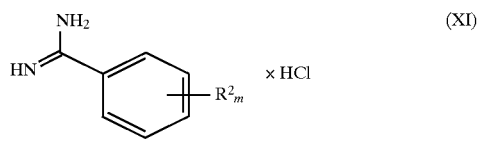

wherein $R^2$ and m are as defined hereinbefore with a compound of formula XII or a salt thereof,

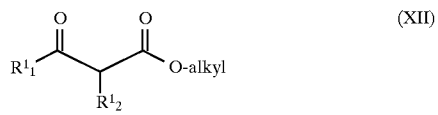

wherein each $R^1_1$ and $R^1_2$ independently are as defined hereinbefore; and the alkyl group is suitably methoxy or ethoxy, to give a pyrimidinone of general formula XIII, in which $R^1$ can also be hydroxyl.

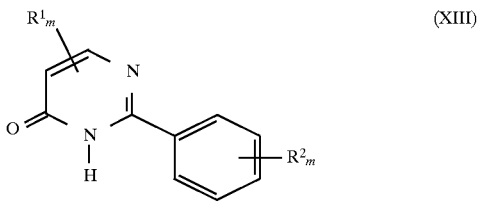

Compounds of general formula XI are known or may be prepared according to procedures described in the art, for example in *Tetrahedron*, 33, 1675f (1979) and *J. Org. Chem.*, 26, 412f. (1960).

The reaction of compounds of formulae XI and XII may be carried out according to *Liebigs Ann.* 1980, 1392f in an organic solvent, suitably an alcohol and preferably ethanol, and in the presence of a base, suitably metal alkoxides, preferably sodium ethoxide.

Compounds of formula XIII may subsequently be converted into compounds of formula III, essentially as described in Davies and Pigott, *J. Chem. Soc.*, 1945, 347, by reaction with a phosphoryl halogenide or thionyl halogenide or phosgene, preferably phosphoryl chloride, phosphoryl bromide, ideally in the absence of a solvent, at elevated temperatures to obtain compounds of formula III.

Compounds of formula III in the meaning above with $R^1$=F may be obtained from compound III when $R^1$ is chlorine or amino according to procedures known in the art, like described in Tullock C. W. et al, *J. Am. Chem. Soc.* 1960, 5197 or Kiburis J. Klister J., *J. Chem. Soc. Chem. Com.* 1969, 381

Compounds of general formula IV are known or may be prepared by known methods. They may be prepared and isolated separately or may be prepared in situ. Generally, a compound of general formula XIV

A—XH (XIV)

wherein A and X are as hereinbefore defined is reacted with a suitable metal base, for example a metal carbonate or hydride. Preferably the metal salt is a sodium or potassium salt.

Compounds of general formula I may, if desired, be isolated and purified using conventional techniques.

The present invention also provides the use of a compound of general formula I as a herbicide. Further, in accordance with the invention there is provided a method of combating undesired plant growth at a locus by treating the locus with a composition according to the invention or a compound of formula I. As a useful action is by foliar spray application, the locus is most suitably the plants in a crop area, typical crops being cereals, maize, soya bean, sunflower or cotton. However, application may also be to the soil for those compounds having pre-emergence herbicidal action. The dosage of active ingredient used may, for example be in the range of from 0.01 to 10 kg/ha, preferably 0.05 to 1kg/ha.

The present invention also extends to a method of making a herbicidal composition of the invention which comprises blending a compound of formula I with at least one carrier.

Preferably there are at least two carriers in a composition of the present invention, at least one of which is a surface-active agent.

A carrier in a composition according to the invention is any material with which the active ingredient is formulated to facilitate application to the locus to be treated, which may be, as appropriate, a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicates such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumaron resins, polyvinyl chloride, and styrene polymers and copolymers; solid polychlorophenols; bitumen; waxes; solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface active agent. For example, the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythrol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or earth alkali metal salts, preferably sodium salts, or sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other active ingredients, for example, compounds possessing insecticidal or fungicidal properties, or other herbicides.

A formulation containing a compound according to the invention can consist of 100 g of active ingredient (compound of formula I), 30 g of dispersing agent, 3 g of antifoaming agent, 2 g of structure agent, 50 g of antifreezing agent, 0.5 g of a biocidal agent and water to 1000 mL. Prior to use it is diluted with water to give the desired concentration of active ingredient.

The following examples illustrate the invention. The structures of the compounds prepared in the following examples were additionally confirmed by NMR and mass spectrometry.

EXAMPLE 1

β-Dimethylamino Propiophenone Hydrochloride

Acetophenone (29.1 mL, 0.25 mol), para-formaldehyde (12.0 g, 0.40 mol) and dimethyl amine hydrochloride (28.5 g, 0.35 mol) are suspended in ethanol (50 mL). Concentrated hydrochloric acid (0.5 mL) is added and the mixture is heated to reflux for 4 hours. Then acetone (200 mL) is added and the resulting clear solution is allowed to cool to ambient temperature. The precipitate is collected by filtration and crystallized from ethanol yielding the title compound (40.7 g, 76.0% of theoretical yield) as colorless crystals with mp. 158° C.

EXAMPLES 2–4

Additional examples of general formula VI are prepared as exemplified by Example 1. Details are given in Table I

TABLE I (VI)

R²—[phenyl]—C(=O)—CH₂—CH₂—N(CH₃)(CH₃) × HCl

| Ex. No. | R² | mp (°C.) | yield (%) |
|---|---|---|---|
| 2 | 3-trifluoromethyl | 157 | 63 |
| 3 | 2,4-dichloro | 136 | 51 |
| 4 | 2,4-dimethyl | 134 | 72 |

EXAMPLE 5

6-Phenyl-2-pyridone

Ethyl 2-chloroacetate (10.6 mL, 0.1 mol) is slowly added to hot (105° C.) pyridine (8.9 mL, 0.11 mol whereby the temperature is maintained in the range of 100° C. to 110° C. The resulting brown oil is dissolved in ethanol (60 mL), β-dimethylamino propiophenone hydrochloride (17.7 g, 0.1 mol; prepared according to Example 1) and ammonium acetate (60 g) are added and the mixture is boiled under reflux for 4 h. After cooling, the mixture is filtered and the solvent is evaporated in vacuo. The residue is crystallized from water, collected by filtration and purified by re-crystallization from toluene. The title compound is obtained as colorless crystals (4.7 g, 28% of th.) with mp. 200° C.

EXAMPLE 6–8

Additional examples are analogously prepared to Example 5. Details are given in Table II.

TABLE II (VIII)

| Ex. No. | R² | mp (°C.) | yield (%) |
|---|---|---|---|
| 6 | 3-trifluoromethyl | 174 | 36 |
| 7 | 2,4-dichloro | 255 | 56 |
| 8 | 2,4-dimethyl | 209 | 23 |

EXAMPLE 9

2-Bromo-6-phenyl pyridine

A mixture of 6-phenyl pyridone (3 g, 17.5 mmol; prepared according to Example 5) and phosphoryl bromide (7.2 g, 25.0 mmol) is heated to 100° C. for 5 h. The cooled mixture is poured into water (40 mL) and the pH is adjusted to 9 by addition of saturated aqueous sodium carbonate. Then the layers are separated and the aqueous layer is extracted with ethyl acetate (50 mL). The combined organic layers are dried with anhydrous magnesium sulphate and the solvent is evaporated in vacuo. The crude product is crystallized from aqueous ethanol. Subsequent purification by flash chromatography (silica gel, hexane/ethyl acetate 9/1 v/v) gives 2-bromo-6-phenyl pyridine (3.1 g, 76% of th.) as light brown crystals with mp 50° C.

EXAMPLES 10–12

Additional compounds of general formula III are prepared by procedures analogous to that of Example 9. Details are given in Table III.

TABLE III (III)

| Ex. No. | R² | mp (°C.) | yield (%) |
|---|---|---|---|
| 10 | 3-trifluoromethyl | oil | 82 |
| 11 | 2,4-dichloro | 123 | 88 |
| 12 | 2,4-dimethyl | oil | 68 |

EXAMPLE 13

2-(1'-Methyl-3'-trifluoromethyl pyrazol-5'-yloxy)-6-phenyl-pyridine

A mixture of 2-bromo-6-phenyl pyridine (0.5 g, 2.1 mmol; prepared according to Example 9), 1-methyl-3-fluoromethyl-5-hydroxypyrazole (0.65 g, 3.9 mmol), potassium carbonate (0.6 g, 4.3 mmol) and N,N-dimethyl formamide (2 mL) is heated to reflux for 12 h. Then the reaction mixture is directly applied onto a flash chromatography column (silica gel). Elution with hexane/ethyl acetate (9/1 v/v) gives the title compound (0.35 g, 52.0% of th.) as light-yellow oil.

EXAMPLES 14–16

The compounds specified in Table IV are obtained by procedures analogous to that of Example 13.

TABLE IV (I)

| Ex. No. | A | R² | mp (°C.) | yield (%) |
|---|---|---|---|---|
| 14 | 1'-CH₃-3'-CF₃-pyrazol-5'-yl | 3"-CF₃ | 113 | 93 |
| 15 | 1'-CH₃-3'-CF₃-pyrazol-5'-yl | 2",4"-dichloro | 91 | 78 |
| 16 | 1'-CH₃-3'-CF₃-pyrazol-5'-yl | 2",4"-dimethyl | oil | 95 |

EXAMPLE 17

2-Fluoro-6-(4¹'-fluorophenyl)-pyridine

Butyl lithium (105.0 mL, 0.26 mol, 2.5M solution in hexane) is added to a solution of 1-bromo-4-fluoro benzene (34.3 mL, 0.31 mol) in anhydrous diethyl ether (200 mL) at −20° C. The mixture is stirred for 60 min and then chilled to -40° C. 2,6-Difluoropyridine (22.7 mL, 0.25 mol) is added and the reaction mixture is allowed to warm to ambient temperature. Subsequently, the mixture is washed with saturated aqueous ammonium chloride (300 mL). The layers are separated and the aqueous layer is washed with diethyl ether 3 times (100 mL each). After drying of the combined organic layers with anhydrous magnesium sulphate, the solvent is removed in vacuo. The crude product is purified by flash column chromatography (silica gel, hexane/AcOEt 8/2) yielding colorless crystals of 2-fluoro-6-(4'-fluorophenyl)-pyridine (19.8 g, 41.0% of th.) with mp 34° C.

EXAMPLE 18

2-Fluoro-6-(4'-fluorophenyl)-4-methylpyridine

A mixture of 2-bromo-6-fluoro-4-methylpyridine (9.5 g, 50 mmol), 4-fluorobenzeneboronic acid (7.8 g, 56 mmol), sodium bicarbonate (12.6 g, 150 mmol), water (200 mL) and catalytic amounts of tetrakis(triphenylphosphine)palladium (0) in DME under nitrogen is heated to reflux overnight. After filtration of the reaction mixture the solvents are removed under reduced pressure. The residue is partitioned between water and ethyl acetate. The layers are separated and the aqueous layer is washed with ethyl acetate. After drying of the combined organic layers with anhydrous magnesium sulphate, the solvent is removed in vacuo. The crude product is purified by flash column chromatography (silica gel, pentane/ethyl acetate 9/1) yielding colorless crystals of 2-fluoro-6-(4'-fluorophenyl)-4-methylpyridine (3.7 g, 36.1% of th.) with mp 49° C.

EXAMPLE 19

2-Fluoro-6-(4'-trifluoromethylphenyl)-3-methylthio-pyridine

To a solution of 2-fluoro-6-(4'-trifluoromethyl-phenyl) pyridine (2.4 g, 10 mmol, prepared according to example 17) in dry THF (35 mL) is added dropwise a solution of 2M LDA in THF (7.5 mL, 15 mmol) at −70° C. After 2 hours at −70° C. dimethyl disulfide (1.41 g, 15 mmol) is added and the reaction mixture is allowed to warm at −20 ° C. The mixture is hydrolysed and extracted with diethylether. After separation the organic layer is dried with anhydrous magnesium sulphate. The solvents are removed and the crude product is purified by flash column chromatography (silica gel). Elution with hexane/ethyl acetate (20/1 v/v) gives the title compound (1.2 g, 42%) with mp 70°–73° C.

EXAMPLES 20–23

Analogously to Example 17, the examples of general formula III are prepared as specified in Table V.

TABLE V

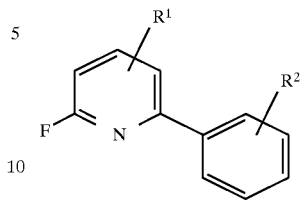

(III)

| Ex. No. | $R^1$ | $R^2$ | mp (°C.) | yield (%) |
|---|---|---|---|---|
| 20 | — | — | oil | 47 |
| 21 | — | 4'-trifluoromethyl | 58 | 75 |
| 22 | — | 3'-trifluoromethyl | oil | 72 |
| 23 | — | 3,4-difluoro | oil | 24 |

EXAMPLE 24

2-(3-Chlorpyrid-5'-yloxy)-6-(4"-fluorophenyloxy)-pyridine

A mixture of 2-fluoro-6-(4'-fluorophenyl)-pyridine (1.9 g, 10.0 mmol, prepared according to Example 17), 3-chloro-5-hydroxypyridine (1.4 g, 11.0 mmol) and potassium carbonate (1.5 g, 11.0 mmol) in sulfolane (10 mL) is heated to reflux for 8 h. The mixture is allowed to cool to ambient temperature and is then filtered through a bed of silica gel which is subsequently washed with ethyl acetate. The organic solutions are combined and the solvent is evaporated in vacuo. The remaining material is applied onto the top of a flash chromatography column (silica gel) and eluted with hexane/ethyl acetate. Elution with hexane/ethyl acetate (8/2 v/v) gives 2-(3'-chlorpyrid-5'-yloxy)-6-(4"-fluorophenyloxy)-pyridine (1.4 g, 46% of th.) as light brown crystals with mp 139° C.

EXAMPLES 25–39

Additional compounds are prepared analogously to example 24. Details are found in Table VI.

TABLE VI

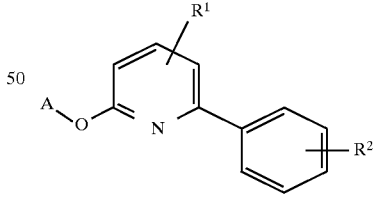

(I)

| Ex. No. | $R^1$ | A | $R^2$ | mp (°C.) | yield (%) |
|---|---|---|---|---|---|
| 25 | — | 3'-CF$_3$-phenyl | 4"-fluoro | oil | 48 |
| 26 | — | 2'-chloropyrid-4'-yl | 4"-fluoro | 137 | 37 |
| 27 | — | 2'-chloropyrid-4'-yl | — | 109 | 35 |
| 28 | — | 2'-chloropyrid-4'-yl | 4"-trifluoro-methyl | 105 | 51 |
| 29 | — | 1'-CH$_3$-3'-CF$_3$-pyrazol-5'-yl | 4"-fluoro | 87 | 44 |
| 30 | — | 1'-CH$_3$-3'-CF$_3$-pyrazol-5'-yl | 4"-trifluoro-methyl | 94 | 59 |
| 31 | — | 1'-CH$_3$-3'-CF$_3$-pyrazol-5'-yl | 3"-trifluoro-methyl | 112 | 44 |

TABLE VI-continued (I)

[Structure: pyridine ring with R¹ substituent, A-O- group, and phenyl with R² substituent]

| Ex. No. | R¹ | A | R² | mp (°C.) | yield (%) |
|---|---|---|---|---|---|
| 32 | — | 2'-chloropyrid-4'-yl | 3"-trifluoromethyl | 92 | 54 |
| 33 | — | 2',4'-difluorophenyl | 3'-trifluoromethyl | oil | 72 |
| 34 | | 3'-CF₃-phenyl | 4"-trifluoromethyl | oil | 44 |
| 35 | 4-CH₃ | 1'-CH₃-3'-CF₃-pyrazol-5'-yl | 4"-fluoro | 85 | 43 |
| 36 | 4-CH₃ | 2'-chloropyrid-4'-yl | 4"-fluoro | 115 | 35 |
| 37 | 3-CH₃S | 3'-CF₃-phenyl | 4"-trifluoromethyl | 133–136 | 67 |
| 38 | 3-CH₃S | 1'-CH₃-3'-CF₃-pyrazol-5'-yl | 4"-trifluoromethyl | 154–156 | 41 |
| 39 | | 1'-CH₃-3'-CF₃-pyrazol-5'-yl | 3",4"-difluoro | oil | 29 |

EXAMPLE 40

4-Fluorobenzamidine Hydrochloride

4-Fluorobenzonitrile (10 g, 83 mmol) is dissolved in a mixture of anhydrous ethanol (5 mL) and diethyl ether (70 mL). The reaction mixture is cooled to ice-bath temperature and saturated with gaseous hydrogen chloride for 90 minutes. The mixture is allowed to warm to ambient temperature and stirred overnight.

The colorless precipitates are filtered off, washed with diethyl ether and dissolved in anhydrous ethanol (20 mL). Diethyl ether (100 mL) saturated with gaseous ammonia is added and the solution is stirred for 3 hours.

The resulting suspension is filtered and the solvent of the filtrate is removed in vacuo. The residue is washed with diisopropyl ether. After drying colourless crystals (5.15 g, 35.5%) of melting point 210° C. are obtained.

EXAMPLES 41 to 50

By methods analogous to that of example 40, further compounds of the general formula XI are prepared. Details are given in table VII.

TABLE VII (XI)

[Structure: benzamidine with R² substituent, × HCl]

| Ex. No. | R² | mp (°C.) | yield (%) |
|---|---|---|---|
| 41 | 4-trifluoromethyl | 167 | 21.4 |
| 42 | 3-methyl | 243 | 29.7 |
| 43 | 3-chloro | 148 | 17.5 |
| 44 | 3,4-difluoro | 185 | 17.4 |

TABLE VII-continued (XI)

[Structure: benzamidine with R² substituent, × HCl]

| Ex. No. | R² | mp (°C.) | yield (%) |
|---|---|---|---|
| 45 | 3-trifluoromethyl | 181 | 17.6 |
| 46 | 3-fluoro | 143 | 20.0 |
| 47 | 4-bromo | 245 | 39 |
| 48 | 4-chloro | >250 | 85 |
| 49 | 4-ᵗbu | 153 | 92 |
| 50 | 4-trifluormethoxy | 210 | 57 |

EXAMPLE 51

2-(4'Fluorophenyl)-5-methyl-4-pyrimidinone

Sodium hydride (0.52 g, 13 mmol) is added to 20 mL of anhydrous ethanol and stirred for 30 minutes at ambient temperature. To this, 4-fluorobenzamidine hydrochloride (1.47 g, 8.5 mmol) (from example 40) is added and the mixture is stirred for further 30 minutes. Methyl 2-formylpropionate (1 g, 10.6 mmol) is added dropwise and the reaction mixture is left for 4 days under stirring at ambient temperature.

After cooling, the solvent is removed in vacuo and the residue is dissolved in aqueous sodium hydroxide (10 mL, 1M). Then the mixture is brought to pH 5 with 2 molar hydrochloric acid. The precipitate is filtered off and washed with diisopropyl ether. After drying, colorless crystals (0.44 g, 10.3%) of melting point >250° C. are obtained.

EXAMPLE 52

6-Hydroxy-2-(4'-trifluoromethylphenyl)-4-pyrimidinone

4-Trifluormethylbenzamidine hydrochloride (22.4 g, 0.1 mol, from example 41) is added to a solution of potassium methylate (0.22 mol) in anhydrous methyl alcohol (65 mL) and stirred for 15 minutes at ambient temperature. Dimethyl malonate (12.6 mL, 0.11 mol) is added and the mixture is heated to reflux for 4 hours. After cooling, the resulting suspension is diluted with methyl alcohol (50 mL).

The solvent is removed in vacuo and the residue is dissolved in water (50 mL). Then the mixture is brought to pH 1 with concentrated hydrochloric acid. The precipitate is filtered off and washed with water. After drying, pale yellow crystals (15.1 g, 59%) of melting point >200° C. are obtained.

EXAMPLE 53

5-Methoxy-2-(4'-trifluoromethylphenyl)-4-pyrimidinone

To a suspension of sodium hydride (60%, 6 g, 0.15 mol) in dry THF (225 mL) a solution of methyl methoxyacetate (14.9 mL, 0.15 mol) in methyl formate (11.1 mL, 0.18 mol) is added during a period of 30 min. The mixture is stirred for 2 hours at ambient temperature. After adding of diethylether (300 mL) the resulting sodium salt of methyl methoxymalonate monoaldehyde can be isolated by suction. Now the sodium salt (0.075 mol) is added to 4-trifluoromethylbenzamidine hydrochloride (16.8 g, 0.075 mol, from example 41) in dry ethyl alcohol (150 mL) and the mixture is stirred for 48 hours at ambient temperature. After heating to reflux for 1 hour water (100 mL) is added to the mixture and the solution is filtered.

The filtrate is brought to pH 5 with acetic acid and the ethyl alcohol is removed in vacuo. The precipitate is filtered off and washed with ethyl alcohol. After drying crystals (13.7 g, 68%) of melting point >200° C. are obtained.

EXAMPLES 54 to 78

By the method exemplified in example 51, further compounds of the general formula III are prepared. Details are given in table VIII.

TABLE VIII (III)

| Ex. No. | $R^1$ | $R^2$ | mp (°C.) | yield (%) |
|---|---|---|---|---|
| 54 | 6-methyl | 4'-fluoro | 267 | 56.8 |
| 55 | 5-methyl | 4'-trifluoromethyl | >250 | 58.7 |
| 56 | 6-methyl | 4'-trifluoromethyl | 209 | 82.2 |
| 57 | 5-methyl | 3'-methyl | 169 | 34.3 |
| 58 | 6-methyl | 3'-methyl | 185 | 41.6 |
| 59 | 5-methyl | 3'-chloro | 260 | 61.4 |
| 60 | 6-methyl | 3'-chloro | 218 | 51 |
| 61 | 5-methyl | 3',4'-difluoro | >250 | 59.4 |
| 62 | 6-methyl | 3',4'-difluoro | 225 | 51.3 |
| 63 | 5-methyl | 3'-trifluoromethyl | 204 | 39.8 |
| 64 | 6-methyl | 3'-trifluoromethyl | 109 | 26.6 |
| 65 | 5,6-dimethyl | 3'-trifluoromethyl | 215 | 70.4 |
| 66 | 5,6-dimethyl | 4'-trifluoromethyl | 242 | 63.4 |
| 67 | 5-methyl | 4'-chloro | >250 | 27.2 |
| 68 | 6-methyl | 4'-chloro | 227 | 6.8 |
| 69 | 5-methyl | 3'-fluoro | 238 | 56 |
| 70 | 6-methyl | 3'-fluoro | 194 | 48.4 |
| 71 | 6-ethyl | 4'-trifluoromethyl | 181 | 87 |
| 72 | 5-methyl | 4'-bromo | >250 | 20 |
| 73 | 6-methyl | 4'-bromo | 245 | 39 |
| 74 | 5-methyl | 4'-$^t$bu | 218 | 81 |
| 75 | 6-methyl | 4'-$^t$bu | 213 | 75 |
| 76 | 5,6-dimethyl | 4'-chloro | 276 | 44 |
| 77 | 5,6-dimethyl | 4'-trifluoromethoxy | 228 | 70 |
| 78 | 6-methyl | 4'-trifluoromethoxy | 196 | 95 |

EXAMPLE 79

2-(4'-Fluorophenyl)-4-chloro-5-methylpyrimidine

A mixture of 2-(4'-fluorophenyl)-5-methyl-4-pyrimidinone (0.79 g, 3.9 mmol) (from example 51) and phosphorous oxychloride (3 mL) is heated to reflux for 1 hour.

The main excess of phosphorous oxychloride is removed in vacuo and the residue is quenched with water (10 mL) to hydrolyze the remaining reagent. The mixture is neutralized and then extracted with ethyl acetate (50 mL). After drying of the organic layer with anhydrous magnesium sulphate, the solvent is removed in vacuo. The title compound (0.63 g, 72.6%) is obtained as colorless crystals of melting point 133°.

EXAMPLE 80

2-(4'-Chlorophenyl)-4,5-dichloro-6-methoxypyrimidine

To a solution of 2-(4'-chlorophenyl)-4,5,6-trichloropyrimidine (1.85 g, 6.3 mmol) in methyl alcohol (30 mL) and THF (60 mL) is added a solution of sodium (0.145 g, 6.3 mmol) in methyl alcohol (10 mL) and the mixture is stirred at ambient temperature overnight. After removal of the solvents in vacuo dichloromethane is added to the residue and the resulting mixture is washed with water. After drying of the organic layer with anhydrous magnesium sulphate, the solvent is removed. Treating of the residue with pentane affords the title compound (1.75 g, 96%) as colorless crystals of melting point 157°–159° C.

EXAMPLES 81–108

The compounds of general formula (III) listed in table IX are prepared analogously to the method of example 79.

TABLE IX (III)

| Ex. No. | $R^1$ | $R^2$ | mp (°C.) | yield (%) |
|---|---|---|---|---|
| 81 | 6-methyl | 4'-fluoro | 143 | 97 |
| 82 | 6-methyl | 4'-trifluoromethyl | 62 | 71.8 |
| 83 | 5-methyl | 4'-trifluoromethyl | 109 | 87.3 |
| 84 | 5-methyl | 3'-methyl | 154 | 98.8 |
| 85 | 6-methyl | 3'-methyl | 134 | 73.7 |
| 86 | 5-methyl | 3'-chloro | 87 | 94.1 |
| 87 | 6-methyl | 3'-chloro | 101 | 26.1 |
| 88 | 5-methyl | 3',4'-difluoro | 114 | 92 |
| 89 | 6-methyl | 3',4'-difluoro | 94 | 90.7 |
| 90 | 5,6-dimethyl | 3'-trifluoromethyl | 83 | 81.6 |
| 91 | 5,6-dimethyl | 4'-trifluoromethyl | 57 | 54.5 |
| 92 | 5-methyl | 3'-trifluoromethyl | 101 | 81.4 |
| 93 | 6-methyl | 3'-trifluoromethyl | 62 | 87.3 |
| 94 | 5-methyl | 4'-chloro | 162 | 85.2 |
| 95 | 6-methyl | 4'-chloro | 101 | 83.6 |
| 96 | 5-methyl | 3'-fluoro | 95 | 83.7 |
| 97 | 6-methyl | 3-fluoro | 86 | 71.5 |
| 98 | 6-ethyl | 4'-trifluoromethyl | 35 | 86 |
| 99 | 5-methyl | 4'-bromo | 156–158 | 94 |
| 100 | 6-methyl | 4'-bromo | 110–112 | 94 |
| 101 | 5-methyl | 4'-$^t$bu | 103–105 | 98 |
| 102 | 6-methyl | 4'-$^t$bu | 70–72 | 99 |
| 103 | 5,6-dimethyl | 4'-chloro | 87 | 71 |
| 104 | 5,6-dimethyl | 4'-trifluoromethoxy | 76 | 81 |
| 105 | 5-methyl | 4'-trifluoromethoxy | 129 | 91 |
| 106 | 6-methyl | 4'-trifluoromethoxy | 64 | 94 |
| 107 | 6-chloro | 4'-trifluoromethyl | 80 | 33 |
| 108 | 5-methoxy | 4'-trifluoromethyl | 108 | 31 |

EXAMPLE 109

2-(4'-Fluorophenyl)-4-(3''-trifluoromethylphenoxy)-6-methylpyrimidine ethyl acetate.

The solvent of the filtrate is removed in vacuo and the residue purified by flash silica gel column chromatography using hexane/ethyl acetate 7/2. Removal of the solvent affords colorless crystals (0.53 g, 56.4%) of melting point 58° C.

EXAMPLES 110–183

Further compounds of the general formula I are prepared by the procedure of example 109. Details are given in table X.

TABLE X

| Ex. No. | R¹ | R² | A | mp (°C.) | yield (%) |
|---|---|---|---|---|---|
| 110 | 5-methyl | 4'-fluoro | 1"-CH₃-3"-CF₃-pyrazol-5"-yl | 133 | 54.7 |
| 111 | 6-methyl | 4'-fluoro | 1"-CH₃-3"-CF₃-pyrazol-5"-yl | 123 | 21 |
| 112 | 6-methyl | 4'-CF₃ | 1"-CH₃-3"-CF₃-pyrazol-5"-yl | 98 | 39.5 |
| 113 | 6-methyl | 4'-CF₃ | 3"-CF₃-phenyl | 89 | 79.9 |
| 114 | 5-methyl | 4'-CF₃ | 1"-CH₃-3"-CF₃-pyrazol-5"-yl | 147 | 27.6 |
| 115 | 5-methyl | 4'-CF₃ | 3"-CF₃-phenyl | 95 | 97.6 |
| 116 | 5-methyl | 3'-CH₃ | 1"-CH₃-3"-CF₃-pyrazol-5"-yl | 121 | 74.9 |
| 117 | 5-methyl | 3'-CH₃ | 3"-CF₃-phenyl | 71 | 74.5 |
| 118 | 6-methyl | 3'-CH₃ | 1"-CH₃-3"-CF₃-pyrazol-5"-yl | 113 | 74.9 |
| 119 | 6-methyl | 3'-CH₃ | 3"-CF₃-phenyl | 60 | 73.2 |
| 120 | 5-methyl | 3'-chloro | 1"-CH₃-3"-CF₃-pyrazol-5"-yl | 116 | 35.4 |
| 121 | 5-methyl | 3'-chloro | 3"-CF₃-phenyl | 105 | 52.4 |
| 122 | 6-methyl | 3'-chloro | 1"-CH₃-3"-CF₃-pyrazol-5"-yl | 96 | 27.1 |
| 123 | 5-methyl | 2',4'-difluoro | 3"-CF₃-phenyl | 68 | 40.4 |
| 124 | 5-methyl | 2',4'-difluoro | 2"-chloropyrid-4"-yl | 148 | 58.8 |
| 125 | 6-methyl | 2',4'-difluoro | 1"-CH₃-3"-CF₃-pyrazol-5"-yl | 78 | 56.4 |
| 126 | 6-methyl | 2',4'-difluoro | 3"-CF₃-phenyl | 64 | 65.3 |
| 127 | 6-methyl | 2',4'-difluoro | 2"-chloropyrid-4"-yl | 162 | 31.7 |
| 128 | 5-methyl | 4'-CF₃ | 2"-chloropyrid-4"-yl | 99 | 44.1 |
| 129 | 5,6-dimethyl | 4'-CF₃ | 1"-CH₃-3"-CF₃-pyrazol-5"-yl | 136 | 13.2 |
| 130 | 5,6-dimethyl | 4'-CF₃ | 3"-CF₃-phenyl | 73 | 65.6 |
| 131 | 5,6-dimethyl | 3'-CF₃ | 1"-CH₃-3"-CF₃-pyrazol-5"-yl | 132 | 30.3 |
| 132 | 5,6-dimethyl | 3'-CF₃ | 3"-CF₃-phenyl | 105 | 67.5 |
| 134 | 6-methyl | 4'-CF₃ | 2",2"-difluoro-1",3"-benzodioxol-4"-yl | 86 | 85 |
| 135 | 6-ethyl | 4'-CF₃ | 1"-CH₃-3"-CF₃-pyrazol-5"-yl | 75 | 46 |
| 136 | 6-ethyl | 4'-CF₃ | 2"-chloropyrid-4"-yl | 97 | 41 |
| 137 | 6-methyl | 3'-CF₃ | 4"-fluorophenyl | 78 | 92 |
| 138 | 6-methyl | 4'-CF₃ | 3"-CF₃-phenyl | 65 | 38 |
| 139 | 5-methyl | 3'-CF₃ | 4"-fluorophenyl | 109–111 | 86 |
| 140 | 5-methyl | 4'-Br | 3"-CF₃-phenyl | 110 | 100 |
| 141 | 6-methyl | 4'-Br | 3"-CF₃-phenyl | 86–88 | 89 |
| 142 | 5-methyl | 4'-ᵗBu | 1"-CH₃-3"-CF₃-pyrazol-5"-yl | 149–151 | 92 |
| 143 | 6-methyl | 4'-ᵗBu | 1"-CH₃-3"-CF₃-pyrazol-5"-yl | 119–121 | 78 |
| 144 | 5-methyl | 4'-ᵗBu | 3"-CF₃-phenyl | 123–124 | 91 |
| 145 | 6-methyl | 4'-ᵗBu | 3"-CF₃-phenyl | oil | 99 |
| 146 | 6-methyl | 4'-Cl | 3"-CF₃-phenyl | 68 | 29 |
| 147 | 5,6-dimethyl | 4'-Cl | 1"-CH₃-3"-CF₃-pyrazol-5"-yl | 142 | 49 |
| 148 | 5,6-dimethyl | 4'-Cl | 2"-chloropyrid-4"-yl | 150 | 36 |
| 149 | 5,6-dimethyl | 4'-Cl | 3"-CF₃-phenyl | 102 | 66 |
| 150 | 5-methyl | | 1"-CH₃-3"-CF₃-pyrazol-5"-yl | 140–150 | 75 |
| 151 | 5,6-dimethyl | 3'-F | 1"-CH₃-3"-CF₃-pyrazol-5"-yl | 117 | 70 |
| 152 | 5-methyl | 4'-Cl | 1"-CH₃-3"-CF₃-pyrazol-5"-yl | 141 | 58 |
| 153 | 5-methyl | 4'-Cl | 2"-chloropyrid-4"-yl | 125 | 31 |
| 154 | 5-methyl | 4'-Cl | 3"-CF₃-phenyl | 101 | 52 |
| 155 | 6-methyl | 4'-Cl | 1"-CH₃-3"-CF₃-pyrazol-5"-yl | 99 | 37 |
| 156 | 6-methyl | 4'-Cl | 2"-chloropyrid-4"-yl | 151 | 8 |
| 157 | 5-methyl | 3',4'-difluoro | 2"-chloropyrid-4"-yl | 146 | 59 |
| 158 | 6-methyl | 3',4'-difluoro | 1"-CH₃-3"-CF₃-pyrazol-5"-yl | 78 | 56 |
| 159 | 6-methyl | 3',4'-difluoro | 3"-CF₃-phenyl | 64 | 65 |
| 160 | 6-methyl | 3',4'-difluoro | 2"-chloropyrid-4"-yl | 162 | 32 |
| 161 | 5-methyl | 4'-CF₃O | 1"-CH₃-3"-CH₃-pyrazol-5"-yl | 117–121 | 58 |
| 162 | 6-methyl | 4'-CF₃O | 1"-CH₃-3"-CH₃-pyrazol-5"-yl | 102–104 | 46 |
| 163 | 5-methyl | 4'-CF₃O | 1"-CH₃-3"-ᵗbu-pyrazol-5"-yl | 96–98 | 58 |
| 164 | 6-methyl | 4'-CF₃O | 1"-CH₃-3"-ᵗbu-pyrazol-5"-yl | 88–89 | 78 |
| 165 | 6-methyl | 4'-CF₃ | 1"-CH₃-3"-ᵗbu-pyrazol-5"-yl | 87–90 | 83 |
| 166 | 6-methyl | 4'-CF₃O | 3"-CF₃-phenyl | 52 | 73 |
| 167 | 6-methyl | 4'-CF₃O | 2"-chloropyrid-4"-yl | 72 | 32 |
| 168 | 5-methyl | 4'-CF₃O | 3"-CF₃-phenyl | 83 | 80 |
| 169 | 5-methyl | 4'-CF₃O | 2"-chloropyrid-4"-yl | 82 | 43 |
| 170 | 5,6-dimethyl | 4'-CF₃O | 3"-CF₃-phenyl | 75 | 66 |
| 171 | 5,6-dimethyl | 4'-CF₃O | 2"-chloropyrid-4"-yl | 107 | 54 |
| 172 | 5-methyl | 3',4'-difluoro | 3"-CF₃-phenyl | 68 | 40 |
| 173 | 6-methyl | 4'-CF₃O | 1"-CH₃-3"-CF₃-pyrazol-5"-yl | 116 | 43 |
| 174 | 5-methyl | 4'-CF₃O | 1"-CH₃-3"-CF₃-pyrazol-5"-yl | 98 | 67 |
| 175 | 5,6-dimethyl | 4'-CF₃O | 1"-CH₃-3"-CF₃-pyrazol-5"-yl | 128 | 45 |
| 176 | 6-methoxy-methyl | 4'-Cl | 2"-chloropyrid-4"-yl | 89–91 | 100 |
| 177 | 6-methoxy-methyl | 4'-Cl | 1"-CH₃-3"-CF₃-pyrazol-5"-yl | 113–115 | 94 |
| 178 | 6-methoxy-methyl | 4'-Cl | 3"-CF₃-phenyl | 140–142 | 92 |
| 179 | 5-methoxy | 4'-CF₃ | 2"-chloropyrid-4"-yl | 96 | 92 |
| 180 | 5-methoxy | 4'-CF₃ | 3"-CF₃-phenyl | 80 | 95 |
| 181 | 5-chloro-6-methoxy | 4'-Cl | 1"-CH₃-3"-CF₃-pyrazol-5"-yl | 173–176 | 95 |
| 182 | 5-chloro-6-methoxy | 4'-Cl | 3"-CF₃-phenyl | 95–98 | 100 |
| 183 | 5-methoxy | 4'-CF₃ | 1"-CH₃-3"-CF₃-pyrazol-5"-yl | 80 | 180 |

EXAMPLE 184

4,6-Bis(2"-chloropyrid-4"-yloxy)-2-(4'-trifluoromethyl-phenyl)pyrimidine

A mixture of 4,6-dichloro-2-(4'-trifluoromethylphenyl) pyrimidine (2.93 g, 10 mmol) (from example 107), 2-chloro- 4-hydroxypyridine (2.85 g, 22 mmol) and potassium carbonate (3.04 g, 22 mmol) in anhydrous N,N-dimethylformamide (20 mL) is heated at 80° C. for 1 hour.

After cooling, the solvent is removed in vacuo, ethyl acetate/hexane 1/1 (10 mL) is added and the suspension is filtered through a bed of silica gel. The resulting solution is washed 3 times with water. After drying of the organic layer with anhydrous magnesium sulphate, the solvent is removed and the residue is purified by flash silica gel chromatography using hexane/ethyl acetate 8/2. Removal of the solvent affords colorless crystals (4.1 g, 86%) of melting point 141° C.

EXAMPLES 185–187

The compounds of general formula (XV a) listed in table XI are prepared analogously to the method of example 184.

TABLE XI (XVa)

| Ex. No. | R² | A | mp (°C.) | yield (%) |
|---|---|---|---|---|
| 185 | 4'-trifluoromethyl | 1"-CH₃-3"-CF₃-pyrazol-5"-yl | 168 | 86 |
| 186 | 4'-trifluoromethyl | 3"-CF₃-phenyl | 92 | 88 |
| 187 | 4'-chloro | 1"-CH₃-3"-CF₃-pyrazol-5"-yl | 156 | 93 |

EXAMPLE 188

6-Methoxy-4-(2"-chloropyrid-4"-yloxy)-2-(4'-trifluoromethylphenyl)pyrimidine 4,6-Bis(2"-chloropyrid-4"-yloxy)-2-(4'-trifluoromethylphenyl)pyrimidine (2.0 g, 4.2 mmol) (from example 184) is dissolved in anhydrous methyl alcohol (5 mL), a solution of potassium methylate (4.2 mmol) in methyl alcohol (1.2 mL) is added dropwise to this solution and the mixture is heated to reflux for 30 min.

The solvent is removed in vacuo and the residue is purified by flash silica gel chromatography using hexane/ethyl acetate 9/1. Removal of the solvents affords colorless crystals (1.0, 62%) of melting point 128° C.

EXAMPLE 189

4,6-Dibromo-2-(4'-trifluoromethylphenyl)pyrimidine

A mixture of 4,6-dihydroxy-2-(4'-trifluoromethylphenyl)pyrimidine (5.12 g, 20 mmol) and phosphorous oxybromide (10 mL) is heated for 3 hours at 100° C. The resulting hot suspension is added to ice and the product can be isolated by suction. After drying, one obtain nearly colorless crystals (6.5 g, 86%) of melting point 87° C.

EXAMPLES 190–201

Compounds of the general formula I are prepared by the procedures of example 188 or 109. Details are given in table XII.

TABLE XII (I)

| Ex. No. | R¹ | R² | A | mp (°C.) | yield (%) |
|---|---|---|---|---|---|
| 190 | 6-methoxy | 4'-CF₃ | 1"-CH₃-3"-CF₃-pyrazol-5"-yl | 130 | 64 |
| 191 | 6-methoxy | 4'-CF₃ | 3"-CF₃-phenyl | 94 | 94 |
| 192 | 6-methylthio | 4'-CF₃ | 1"-CH₃-3"-CF₃-pyrazol-5"-yl | 127 | 55 |
| 193 | 6-methylthio | 4'-CF₃ | 2"-chloropyrid-4"-yl | 106 | 41 |
| 194 | 6-dimethyl-amino | 4-CF₃ | 1"-CH₃-3"-CF₃-pyrazol-5"-yl | 148 | 90 |
| 195 | 6-ethylamino | 4-CF₃ | 1"-CH₃-3"-CF₃-pyrazol-5"-yl | 102 | 23 |
| 196 | 6-methoxy | 4'-Cl | 1"-CH₃-3"-CF₃-pyrazol-5"-yl | 144 | 80 |
| 197 | 6-methoxy-amino | 4'-Cl | 1"-CH₃-3"-CF₃-pyrazol-5"-yl | 178 | 16 |
| 198 | 6-dimethyl-amino | 4'-Cl | 1"-CH₃-3"-CF₃-pyrazol-5"-yl | 143 | 13 |
| 199 | 6-amino | 4'-Cl | 1"-CH₃-3"-CF₃-pyrazol-5"-yl | 149 | 80 |
| 200 | 6-methyl-amino | 4'-Cl | 1"-CH₃-3"-CF₃-pyrazol-5"-yl | 114 | 97 |
| 201 | 6-bromo | 4'-CF₃ | 1"-CH₃-3"-CF₃-pyrazol-5"-yl | 110 | 57 |
| 202 | 6-chloro | 4'-Cl | 1"-CH₃-3"-CF₃-pyrazol-5"-yl | 122 | 26 |
| 203 | 6-chloro | 4'-CF₃ | 1"-CH₃-3"-CF₃-pyrazol-5"-yl | 113 | 69 |

EXAMPLE 204

6-Vinyl-4-(1"-methyl-3"-trifluoromethylpyrazol-5"-yl)-2-(4'-trifluoromethylphenyl)pyrimidine A mixture of 6-bromo-4-(1"-methyl-3"-trifluoromethylpyrazol-5"-yl)-2-(4'-trifluoromethylphenyl)pyrimidine (2 g, 4.3 mmol, from example 201), vinyltributylstannate (1.4 mL, 4.7 mmol), tetrakis (triphenylphosphine)-palladium(0) (0.1 g, 0.09 mmol), toluene (20 mL) and 3 crystals of 2,6-ditertbutyl-4-methylphenol is heated to reflux for 90 min. After cooling, a 1.2N solution of pyridinium fluoride in THF/pyridine (4 mL) and pyridine (2 mL) is added. The solution is stirred for 17 hours at ambient temperature. To the resulting mixture ethyl acetate (100 mL) is added and the solution is washed twice with water and a saturated solution of sodium bicarbonate. After drying of the organic layer with anhydrous magnesium sulphate, the solvent is removed and the residue is purified by flash silica gel chromatography using hexane/ethyl acetate 7/3. Removal of the solvent affords nearly colorless crystals (1.45 g, 82%) of melting point 112° C.

EXAMPLES 205–214

Additional compounds are prepared analogously to example 24. Details are found in Table XIII.

TABLE XIII (Structure I: pyridine with R¹ at 4-position, A-O- at 2-position, and aryl-R² at 6-position)

| Ex. No. | R¹ | A | R² | mp (°C.) |
|---|---|---|---|---|
| 205 | 3-ethyl | 3'-CF$_3$-phenyl | 4"-trifluoromethyl | 72–75 |
| 206 | 5-ethyl | 3'-CF$_3$-phenyl | 4"-trifluoromethyl | 44–46 |
| 207 | 4-methyl | 1'-CH$_3$-3'-CF$_3$-pyrazol-5'-yl | 4"-trifluoromethyl | 98 |
| 208 | 4-methyl | 3'-CF$_3$-phenyl | 4"-trifluoromethyl | oil |
| 209 | 4-methyl | 1'-CH$_3$-3'-CF$_3$-pyrazol-5'-yl | 3",5"-dichloro | 117 |
| 210 | 4-methyl | 1'-CH$_3$-3'-CF$_3$-pyrazol-5'-yl | 3",5"-di(trifluoromethyl) | 126 |
| 211 | 4-methyl | 1'-CH$_3$-3'-CF$_3$-pyrazol-5'-yl | 3"-chloro-4"-fluoro | 101 |
| 212 | 4-methyl | 1'-CH$_3$-3'-CF$_3$-pyrazol-5'-yl | 3",4"-dichloro | 97 |
| 213 | 3-methyl | 3'-CF$_3$-phenyl | 4"-trifluoromethyl | 71–73 |
| 214 | 3-methyl | 1'-CH$_3$-3'-CF$_3$-pyrazol-5'-yl | 4"-trifluoromethyl | 130–133 |

EXAMPLES 215–217

Additional compounds are prepared analogously to example 188 starting with 2,4-bisaryloxy-6-arylpyridines. Details are found in Table XIV.

TABLE XIV (Structure I)

| Ex. No. | R¹ | A | R² | mp (°C.) |
|---|---|---|---|---|
| 215 | 4-methoxy | 1'-CH$_3$-3'-CF$_3$-pyrazol-5'-yl | 4"-trifluoromethyl | 102 |
| 216 | 4-methyl-amino | 1'-CH$_3$-3'-CF$_3$-pyrazol-5'-yl | 4"-trifluoromethyl | 168 |
| 217 | 4-methoxy | 3'-CF$_3$-phenyl | 4"-trifluoromethyl | oil |

The required 2,4-bisaryloxy-6-arylpyridines are obtained in analogous way as explicitly described below for:

2,4-Bis-(1"-methyl-3"-trifluoromethylpyrazol-5"-yloxy)-6-(4'-trifluoromethylphenyl)pyridine A mixture of 4-nitro-2,6-dichloropyridine (3.9 g, 20 mmol), 1-methyl-3-trifluoromethyl-5-hydroxypyrazole (7.3 g, 44 mmol) and potassium carbonate (6.7 g, 48 mmol) in anhydrous sulfolane is heated to 110° C. overnight. The reaction mixture is cooled to ambient temperature, diluted with pentane/ethyl acetate (volume ratio of 1:1) and filtered through a bed of silica gel. The filtrate is washed 10 times with water, dried over anhydrous magnesium sulfate and the solvents are removed in vacuo. The residue is purified by flash silica gel chromatography using pentane/ethyl acetate.

One obtains 2,4-bis-(1'-methyl-3'-trifluoromethylpyrazol-5'-yloxy)-6-chloropyridine (4.3 g, m.p. 105° C.).

A mixture of bis(benzonitrile)palladium(II)chloride (0.19 g, 0.5 mmol) and 1,4-bis(diphenylphosphino)butane (0.2 g, 0.5 mmol) in anhydrous toluene (10 mL) is heated to reflux under a atmosphere of nitrogen. After 2 hours 4-trifluoromethylbenzeneboronic acid (1.2 g, 6.5 mmol), 2,4-bis-(1"-methyl-3"-trifluoromethylpyrazol-5"-yloxy)-6-chloropyridine (2.2 g, 5 mmol). ethanol (2.5 mL) and a 1M hydrous solution of sodium carbonate (5 mL) is added and the mixture is heated to reflux for additional 2 hours under a nitrogen atmosphere. The reaction mixture is diluted with ethyl acetate and filtered through a bed of silica gel. The filtrate is washed with water, dried over anhydrous magnesium sulfate and the solvents are removed in vacuo. The residue is purified by flash silica gel chromatography using pentane/ethyl acetate (volume ratio 8/2). One obtain colorless crystals of the title compound (2 g, 73% yield) of melting point 133° C.

EXAMPLES 218–287

Further compounds of the general formula I are prepared by the procedure of example 109. Details are given in table XV.

TABLE XV (Structure I)

| Ex. No. | R¹ | R² | A | mp (°C.) |
|---|---|---|---|---|
| 218 | 5-methyl | 4'-CF$_3$ | 4"-chloro-pyrimidine-6"-yl | 107 |
| 219 | 6-methylthio | 4'-chloro | 1"-CH$_3$-3"-CF$_3$-pyrazol-5"-yl | 131 |
| 220 | 6-bromo | 4'-CF$_3$ | 2"-chloro-pyridine-4"-yl | 108 |
| 221 | 6-bromo | 4'-CF$_3$ | 3"-CF$_3$-phenyl | 96 |
| 222 | 6-(dimethyl-amino)-methyleneamino | 4'-chloro | 1"-CH$_3$-3"-CF$_3$-pyrazol-5"-yl | 126 |
| 223 | 6-ethinyl | 4'-CF$_3$ | 1"-CH$_3$-3"-CF$_3$-pyrazol-5"-yl | 117 |
| 224 | 6-methoxy-methyl | 4'-CF$_3$ | 1"-CH$_3$-3"-CF$_3$-pyrazol-5"-yl | 114–116 |
| 225 | 6-methoxy-methyl | 4'-CF$_3$ | 3"-CF$_3$-4"-fluorophenyl | 71–73 |
| 226 | 6-methoxy-methyl | 4'-CF$_3$ | 2"-chloro-pyridine-4"-yl | 100–102 |
| 227 | 4,5-dichloro | 4'-chloro | 1"-CH$_3$-3"-CF$_3$-pyrazol-5"-yl | 156–160 |
| 228 | 6-methyl | 4'-SO$_2$CH$_3$ | 1"-CH$_3$-3"-CF$_3$-pyrazol-5"-yl | 132 |
| 229 | 6-methyl | 4'-SO$_2$CH$_3$ | 3"-CF$_3$-phenyl | 162 |
| 230 | 6-methyl | 4'-SO$_2$CH$_3$ | 2"-chloro-pyrid-4"-yl | 168 |
| 231 | 4-fluoro | 4'-CF$_3$ | 1"-CH$_3$-3"-CF$_3$-pyrazol-5"-yl | 124 |
| 232 | 6-ethyl | 4'-CF$_3$ | 1"-CH$_3$-3"-CF$_3$-pyrazol-5"-yl | 90 |
| 233 | 6-ethyl | 4'-CF$_3$ | 3"-CF$_3$-phenyl | 77 |
| 234 | 6-ethyl | 4'-CF$_3$ | 2"-chloro-pyrid-4"-yl | 97 |
| 235 | 6-ethyl | 4'-CF$_3$ | 4"-chloro-pyrimidine-6"-yl | 86 |

TABLE XV-continued

Structure (I): pyridine with R¹ substituent, A-O- group, and phenyl with R² substituent.

| Ex. No. | R¹ | R² | A | mp (°C.) |
|---|---|---|---|---|
| 236 | 6-ethyl | 4'-CF₃ | 6"-(2,2,2-trifluoro-ethoxy)-pyrimidine-4"-yl | 105 |
| 237 | 6-ethyl | 4'-CF₃ | 2",6"-dichloro-pyrid-4"-yl | 158 |
| 238 | 6-ethyl | 4'-CF₃ | 6"-cyano-pyrid-4"-yl | 130 |
| 239 | 6-ethyl | 4'-CF₃ | 3"-CF₃-4"-fluoro-phenyl | 62 |
| 240 | 4-chloro | 4'-CF₃ | 3"-CF₃-phenyl | 89 |
| 241 | 4-chloro | 4'-CF₃ | 2"-chloro-pyrid-4"-yl | 104 |
| 242 | 4-chloro | 4'-CF₃ | 1"-CH₃-3"-C₂F₅-pyrazol-5"-yl | 108 |
| 243 | 6-methyl | 4'-CF₃ | 2"-difluoromethoxy-pyrid-4"-yl | 89–92 |
| 244 | 4-methylamino | 4'-CF₃ | 1"-CH₃-3"-CF₃-pyrazol-5"-yl | 167 |
| 245 | 6-ethoxy | 4'-CF₃ | 1"-CH₃-3"-CF₃-pyrazol-5"-yl | 162 |
| 246 | 6-(2-fluoro-ethoxy) | 4'-CF₃ | 1"-CH₃-3"-CF₃-pyrazol-5"-yl | 148 |
| 247 | 6,(2,2,2-trifluoroethoxy) | 4'-CF₃ | 1"-CH₃-3"-CF₃-pyrazol-5"-yl | 133 |
| 248 | 6-allyloxy | 4'-CF₃ | 1"-CH₃-3"-CF₃-pyrazol-5"-yl | 127 |
| 249 | 5,6-diethoxy | 4'-CF₃ | 1"-CH₃-3"-CF₃-pyrazol-5"-yl | 93 |
| 250 | 6-methoxymethyl | 4"-CF₃ | 3"-CF₃-phenyl | 56–59 |
| 251 | 6-cyanomethyl | 4'-CF₃ | 1"-CH₃-3"-CF₃-pyrazol-5"-yl | 127–130 |
| 252 | 6-hydrazino | 4'-CF₃ | 1"-CH₃-3"-CF₃-pyrazol-5"-yl | 187 |
| 253 | 4-fluoro | 4'-CF₃ | 3"-CF₃-phenyl | oil |
| 254 | 4-fluoro | 4'-CF₃ | 2"-chloropyrid-4"-yl | 136 |
| 255 | 4-iodo | 4'-CF₃ | 1"-CH₃-3"-CF₃-pyrazol-5"-yl | 108 |
| 256 | 6-methyl | 4'-CHCl₂ | 1"-CH₃-3"-CF₃-pyrazol-5"-yl | 116 |
| 257 | 6-difluoro-methoxy | 4'-CF₃ | 3"-CF₃-phenyl | 92–95 |
| 258 | 4-chloro-5-methyl | 4'-CF₃ | 1"-CH₃-3"-CF₃-pyrazol-5"-yl | 146 |
| 259 | 4-fluoro-5-methyl | 4'-CF₃ | 1"-CH₃-3"-CF₃-pyrazol-5"-yl | 150 |
| 260 | 4-fluoro-5-methyl | 4'-CF₃ | 3"-CF₃-phenyl | 69 |
| 261 | 4-fluoro-5-methyl | 4'-CF₃ | 2"-chloropyrid-4"-yl | 129 |
| 262 | 6-methyl | 4'-CF₃ | 2"-trifluoromethyl-pyrid-4"-yl | 105 |
| 263 | 6-methyl | 4'-CN | 1"-CH₃-3"-CF₃-pyrazol-5"-yl | 177 |
| 264 | 5-chloro | 4'-CF₃ | 1"-CH₃-3"-CF₃-pyrazol-5"-yl | 135–140 |
| 265 | 6-methyl | 4'-CF₃ | 2"-(2,2,2-trifluoro-ethoxy)pyrid-4"-yl | 104–106 |
| 266 | 4-chloro | 4'-CF₃ | 2"-difluoromethoxy-pyrid-4"-yl | 101–104 |
| 267 | 6-methyl | 4'-CF₃ | 3"-CN-phenyl | 138 |
| 268 | 5-isopropyl | 4'-CF₃ | 3"-CF₃-phenyl | 66 |
| 269 | 6-methoxy | 4'-CF₃ | 2"-trifluoromethyl-pyrid-4"-yl | 84 |
| 270 | 5-methyl | 4'-CF₃ | 2"-trifluoromethyl-pyrid-4"-yl | 109 |
| 271 | 4-chloro | 4'-CF₃ | 2"-trifluoromethyl-pyrid-4"-yl | 97 |
| 272 | 6-methyl | 4',5'-di(CF₃) | 1"-CH₃-3"-CF₃-pyrazol-5"-yl | 132 |
| 273 | 6-methyl | 4',5'-di(CF₃) | 3"-CF₃-phenyl | 93 |
| 274 | 6-methyl | 4',5'-di(CF₃) | 2"-chloropyrid-4"-yl | 128 |
| 275 | 4-difluoro-methoxy | 4'-CF₃ | 1"-CH₃-3"-CF₃-pyrazol-5"-yl | 108–110 |
| 276 | 6-methoxy | 4'-CF₃ | 2"-difluoromethoxy-pyrid-4"-yl | 88–91 |
| 277 | 5-methyl | 4'-CF₃ | 2"-difluoromethoxy-pyrid-4"-yl | 101–103 |
| 278 | 4-chloro | 4'-CF₃ | 2"-(2,2,2-trifluoro-ethoxy)pyrid-4"-yl | 98–101 |
| 279 | 6-methoxy | 4'-CF₃ | 2"-(2,2,2-trifluoro-ethoxy)pyrid-4"-yl | 91–94 |
| 280 | 5-methyl | 4'-CF₃ | 2"-(2,2,2-trifluoro-ethoxy)pyrid-4"-yl | 74–76 |
| 281 | 5-methyl | 4'-CF₃ | 3"-CF₃O-phenyl | 73 |
| 282 | 6-methyl | 4'-CF₃ | 3"-CF₃O-phenyl | 63 |
| 283 | 5-methyl | 4'-CF₃ | 2"-cyanopyrid-4"-yl | 133 |
| 284 | 5-methyl | 4'-CF₃ | 2"-pentafluoroethyl-pyrid-4"-yl | 134 |
| 285 | 6-methyl | 4'-CF₃ | 2"-pentafluoroethyl-pyrid-4"-yl | 91 |
| 286 | 6-methoxy-methyl | 4'-CF₃ | 2"-trifluoromethyl-pyrid-4"-yl | 70 |
| 287 | 6-methoxy | 4'-CF₃ | 2"-pentafluoroethyl-pyrid-4"-yl | 100 |

EXAMPLE 288

Herbicidal Activity

To evaluate their herbicidal activity, compounds according to the invention are tested using a representative range of plants:

TRZAS *Triticum aestivum*
HORVW *Hordeum vulgare*
GOSHI *Gossypium hirsutum*
HELAN *Helianthus annuus*
ORYSA *Oryza sativa*
GLXMA *Glycine max*
BEAVA *Beta vulgaris*
ZEAMX *Zea mays*
ALOMY *Alopecurus myosuroides*
AVEFA *Avena fatua*
ECHCG *Echinocloa crus-galli*
SETVI *Setaria viridis*
GALAP *Galium aparine*
STEME *Stellaria media*
CHEAL *Chenopodium album*
VERPE *Veronica persica*
LAMPU *Lamium purpureum*
VIOAR *Viola arvensis*
SIDSP *Sida spinosa*
AMBAR *Ambrosia artemisifolia*

ABUTH *Abutilon theophrasti*
IPOPU *Ipomoea purpurea*
SINAL *Sinapis alba*
AMARE *Amaranthus retroflexus*

The tests fall into two categories, pre-emergence and post-emergence. The pre-emergence tests involve spraying a liquid formulation of the compound onto the soil in which the seeds of the plant species mentioned above had recently be sown. The post-emergence tests involve spraying seedlings of the above species with a such a formulation.

The soil used in the tests is a prepared horticultural loam. The formulations used in the test are prepared from solutions of the test compounds in acetone containing 0.4% by weight of an alkylphenyl/ethylene oxide condensate surfactant available under the trade mark TRITON X 155. The acetone solutions are diluted with water and the resulting formulations at dosage levels corresponding to 1000 g or 300 g of active material per hectare in a volume equivalent to 400 liters per hectare. In the pre-emergence tests untreated sown soil and in the post-emergence tests untreated soil bearing untreated seedling plants are used as controls.

The herbicidal effects of the test compounds are assessed visually twenty days after spraying the foliage and the soil (in the case of examples 13–16 thirteen days after treatment) and are recorded on a 0–9 scale. A rating 0 indicates growth as untreated control, a rating 9 indicates death. An increase of 1 unit on the linear scale approximates to a 10% increase in the level of effect. An asterisk indicates that the specified plant species was not treated in the test.

The results of the test are set out in the table shown below in which the compounds are identified by reference to the preceding examples. An asterisk indicates that the specified plant species was not treated in the test.

| Ex. No | dose g/ha | appl. time | TRZAW | HORVW | GOSHI | HELAN | ORYSA | GLXMA | BEAVA | ZEAMX | ALOMY | AVEFA | ECHCG | SETVI |
|---|---|---|---|---|---|---|---|---|---|---|---|---|---|---|
| 13 | 100 | pre | * | * | * | * | 0 | 0 | 4 | 2 | * | 2 | 4 | * |
|    | 0   | post | * | * | * | * | 2 | 5 | 8 | 4 | * | 2 | 5 | * |
| 14 | 100 | pre | * | * | * | * | 3 | 4 | 9 | 9 | * | 6 | 8 | * |
|    | 0   | post | * | * | * | * | 4 | 6 | 9 | 6 | * | 6 | 7 | * |
| 15 | 100 | pre | * | * | * | * | 0 | 2 | 8 | 2 | * | 2 | 5 | * |
|    | 0   | post | * | * | * | * | 2 | 6 | 9 | 5 | * | 2 | 7 | * |
| 16 | 100 | pre | * | * | * | * | 0 | 0 | 2 | 0 | * | 0 | 2 | * |
|    | 0   | post | * | * | * | * | 0 | 2 | 7 | 4 | * | 2 | 2 | * |
| 24 | 300 | pre | 1 | 0 | 0 | 0 | * | * | * | 0 | 0 | * | * | 0 |
|    |     | post | 0 | 0 | 1 | 1 | * | * | * | 1 | 0 | * | * | 0 |
| 25 | 300 | pre | 0 | 0 | 0 | 0 | * | * | * | 0 | 0 | * | * | 1 |
|    |     | post | 0 | 0 | 1 | 2 | * | * | * | 2 | 0 | * | * | 0 |
| 26 | 300 | pre | 1 | 0 | * | 1 | * | * | * | 1 | * | * | * | 0 |
|    |     | post | 1 | 2 | * | 3 | * | * | * | 2 | * | * | * | 0 |
| 27 | 300 | pre | 0 | 0 | * | 0 | * | * | * | 0 | * | * | * | 0 |
|    |     | post | 2 | 2 | * | 3 | * | * | * | 3 | * | * | * | 1 |
| 28 | 300 | pre | 0 | 3 | 0 | 0 | * | * | * | 3 | 5 | * | 6 | 9 |
|    |     | post | 3 | 3 | 4 | 5 | * | * | * | 4 | 5 | * | 4 | 6 |
| 29 | 300 | pre | 0 | 1 | * | 0 | * | * | * | 0 | * | * | * | 8 |
|    |     | post | 4 | 3 | * | 4 | * | * | * | 3 | * | * | * | 3 |
| 30 | 300 | pre | 4 | 6 | 3 | 3 | * | * | * | 4 | 9 | * | 8 | 9 |
|    |     | post | 4 | 5 | 6 | 6 | * | * | * | 4 | 6 | * | 6 | 7 |
| 31 | 300 | pre | 1 | 4 | 2 | 0 | * | 3 | * | 1 | 8 | * | 5 | 9 |
|    |     | post | 3 | 5 | 8 | 5 | * | 5 | * | 8 | 7 | * | 4 | 7 |
| 32 | 300 | pre | 1 | 0 | 0 | 0 | * | 0 | * | 0 | 3 | * | 2 | 8 |
|    |     | post | 2 | 2 | 5 | 4 | * | 3 | * | 3 | 3 | * | 2 | 4 |
| 33 | 300 | pre | 2 | 0 | 0 | 0 | * | 2 | * | 0 | 0 | * | 0 | 0 |
|    |     | post | 0 | 0 | 0 | 0 | * | 0 | * | 0 | 0 | * | 0 | 2 |
| 34 | 300 | pre | 1 | 3 | 3 | * | 3 | 1 | * | 2 | 7 | * | 8 | 8 |
|    |     | post | 2 | 2 | 5 | * | 2 | 7 | * | 2 | 4 | * | 4 | 5 |
| 39 | 300 | pre | 1 | 3 | 0 | * | * | 0 | * | 0 | 5 | * | 4 | 9 |
|    |     | post | 1 | 2 | 4 | * | * | 3 | * | 3 | 3 | * | 2 | 7 |
| 109 | 300 | pre | 0 | 0 | 0 | 0 | * | * | * | 0 | 0 | * | 0 | 0 |
|    |     | post | 0 | 0 | 2 | 0 | * | * | * | 0 | 0 | * | 0 | 1 |
| 110 | 300 | pre | 3 | 4 | 2 | 1 | * | * | * | 2 | 8 | * | 6 | 9 |
|    |     | post | 4 | 5 | 6 | 6 | * | * | * | 4 | 7 | * | 7 | 6 |
| 111 | 300 | pre | 1 | 3 | 0 | 0 | * | * | * | 0 | 8 | * | * | 9 |
|    |     | post | 3 | 3 | 5 | 5 | * | * | * | 4 | 4 | * | * | 6 |
| 112 | 300 | pre | 3 | 5 | 6 | 3 | * | 5 | * | 4 | 9 | * | 8 | 9 |
|    |     | post | 4 | 5 | 8 | 8 | * | 8 | * | 5 | 7 | * | 6 | 8 |
| 113 | 300 | pre | 3 | 6 | 6 | 2 | * | 3 | * | 3 | 9 | * | 8 | 9 |
|    |     | post | 4 | 5 | 8 | 8 | * | 8 | * | 5 | 6 | * | 7 | 9 |
| 114 | 300 | pre | 4 | 5 | 8 | 3 | * | 4 | * | 3 | 8 | * | 8 | 9 |
|    |     | post | 4 | 5 | 8 | 6 | * | 6 | * | 6 | 8 | * | 5 | 8 |
| 115 | 300 | pre | 4 | 7 | 8 | 3 | * | 5 | * | 4 | 8 | * | 8 | 9 |
|    |     | post | 4 | 6 | 9 | 8 | * | 8 | * | 6 | 7 | * | 6 | 8 |
| 116 | 300 | pre | 0 | 3 | 0 | 0 | * | 0 | * | 0 | 6 | * | 4 | 9 |
|    |     | post | 2 | 3 | 4 | 4 | * | 5 | * | 3 | 3 | * | 2 | 8 |
| 117 | 300 | pre | 0 | 2 | 0 | 0 | * | 0 | * | 2 | 7 | * | 5 | 9 |
|    |     | post | 3 | 3 | 4 | 4 | * | 4 | * | 4 | 4 | * | 3 | 4 |
| 118 | 300 | pre | 0 | 0 | 0 | 0 | * | 0 | * | 0 | 3 | * | 4 | 7 |
|    |     | post | 0 | 2 | 4 | 4 | * | 3 | * | 2 | 3 | * | 3 | 4 |
| 119 | 300 | pre | 0 | 0 | 0 | 0 | * | 0 | * | 0 | 0 | * | 1 | 0 |
|    |     | post | 0 | 2 | 0 | 2 | * | 1 | * | 1 | 1 | * | 0 | 1 |

-continued

| | | | | | | | | | | | | | | |
|---|---|---|---|---|---|---|---|---|---|---|---|---|---|---|
| 120 | 300 | pre | 1 | 3 | 2 | 0 | * | 0 | * | 2 | 8 | * | 6 | 9 |
| | | post | 2 | 4 | 5 | 4 | * | 5 | * | 3 | 5 | * | 4 | 5 |
| 121 | 300 | pre | 2 | 3 | 2 | 0 | * | 1 | * | 3 | 8 | * | 7 | 9 |
| | | post | 3 | 4 | 8 | 4 | * | 5 | * | 5 | 5 | * | 6 | 7 |
| 122 | 300 | pre | * | * | * | * | * | * | * | * | * | * | * | * |
| | | post | * | * | * | * | * | * | * | * | * | * | * | * |
| 123 | 300 | pre | 0 | 0 | 0 | 0 | * | 0 | * | 0 | 0 | * | 0 | 0 |
| | | post | 1 | 1 | 2 | 3 | * | 2 | * | 1 | 1 | * | 2 | 2 |
| 124 | 300 | pre | 1 | 3 | 2 | 1 | * | 5 | * | 5 | 5 | * | 6 | 8 |
| | | post | 4 | 4 | 6 | 5 | * | 5 | * | 5 | 5 | * | 6 | 7 |
| 125 | 300 | pre | 3 | 4 | 3 | 2 | * | 3 | * | 5 | 8 | * | 7 | 9 |
| | | post | 4 | 5 | 5 | 5 | * | 6 | * | 5 | 5 | * | 6 | 7 |
| 126 | 300 | pre | 0 | 0 | 0 | 0 | * | 0 | * | 0 | 3 | * | 0 | 9 |
| | | post | 2 | 2 | 5 | 4 | * | 3 | * | 3 | 3 | * | 3 | 3 |
| 127 | 300 | pre | 0 | 0 | 1 | 0 | * | 0 | * | 2 | 2 | * | 0 | 8 |
| | | post | 0 | 1 | 4 | 3 | * | 2 | * | 2 | 3 | * | 2 | 4 |
| 128 | 300 | pre | 4 | 5 | 7 | 2 | * | 3 | * | 5 | 8 | * | 7 | 9 |
| | | post | 2 | 5 | 6 | 5 | * | 5 | * | 6 | 6 | * | 7 | 7 |
| 129 | 300 | pre | 3 | 3 | 5 | 4 | * | 3 | * | 3 | 8 | * | 6 | 9 |
| | | post | 2 | 4 | 7 | 5 | * | 5 | * | 3 | 5 | * | 5 | 6 |
| 130 | 300 | pre | 2 | 5 | 3 | 2 | * | 3 | * | 3 | 7 | * | 6 | 9 |
| | | post | 2 | 4 | 6 | 5 | * | 5 | * | 4 | 5 | * | 5 | 7 |
| 131 | 300 | pre | 0 | 0 | 2 | 2 | * | 0 | * | 2 | 1 | * | 0 | 8 |
| | | post | 1 | 1 | 3 | 4 | * | 2 | * | 1 | 2 | * | 2 | 2 |
| 132 | 300 | pre | 0 | 0 | 0 | 0 | * | 3 | * | 0 | 0 | * | 0 | 3 |
| | | post | 0 | 1 | 3 | 2 | * | 2 | * | 1 | 0 | * | 1 | 2 |
| 133 | 400 | pre | 5 | 5 | * | * | 5 | 7 | * | 4 | 8 | * | * | 9 |
| | | post | 3 | 4 | * | * | 5 | 6 | * | 4 | 8 | * | * | 8 |
| 134 | 400 | pre | 3 | 4 | * | * | 3 | 4 | * | 4 | 8 | * | * | 9 |
| | | post | 2 | 3 | * | * | 2 | 6 | * | 3 | 4 | * | * | 8 |
| 135 | 300 | pre | 6 | 7 | * | * | 5 | 4 | * | 3 | 8 | * | 8 | 9 |
| | | post | 4 | 6 | * | * | 4 | 6 | * | 3 | 7 | * | 6 | 7 |
| 136 | 300 | pre | 6 | 8 | * | * | 5 | 4 | * | 4 | 8 | * | 8 | 8 |
| | | post | 5 | 6 | * | * | 5 | 6 | * | 4 | 6 | * | 7 | 7 |
| 137 | 300 | pre | 0 | 0 | * | * | 0 | 0 | * | 0 | 0 | * | 0 | 0 |
| | | post | 0 | 1 | * | * | 1 | 1 | * | 0 | 1 | * | 0 | 0 |
| 138 | 300 | pre | 6 | 7 | * | * | 4 | 4 | * | 3 | 8 | * | 8 | 9 |
| | | post | 4 | 7 | * | * | 4 | 7 | * | 3 | 6 | * | 6 | 7 |
| 139 | 300 | pre | 0 | 0 | * | * | 0 | 0 | * | 0 | 0 | * | 0 | 0 |
| | | post | 1 | 2 | * | * | 1 | 2 | * | 0 | 1 | * | 1 | 1 |
| 140 | 300 | pre | 4 | 5 | 5 | * | 3 | 2 | * | 2 | 8 | * | 8 | 8 |
| | | post | 3 | 4 | 5 | * | 5 | 5 | * | 3 | 7 | * | 4 | 8 |
| 141 | 300 | pre | 1 | 4 | 2 | * | 2 | 1 | * | 2 | 7 | * | 8 | 9 |
| | | post | 2 | 3 | 9 | * | 2 | 4 | * | 3 | 4 | * | 3 | 5 |
| 142 | 300 | pre | 0 | 0 | 1 | * | 0 | 1 | * | 0 | 0 | * | 1 | 5 |
| | | post | 0 | 1 | 5 | * | 0 | 4 | * | 2 | 0 | * | 1 | 1 |
| 143 | 300 | pre | 0 | 1 | 4 | * | 2 | 2 | * | 2 | 6 | * | 5 | 8 |
| | | post | 1 | 2 | 8 | * | 0 | 3 | * | 3 | 1 | * | 2 | 3 |
| 144 | 300 | pre | 0 | 0 | 4 | * | 0 | 2 | * | 0 | 0 | * | 0 | 3 |
| | | post | 1 | 1 | 6 | * | 0 | 3 | * | 2 | 0 | * | 1 | 1 |
| 145 | 300 | pre | 0 | 0 | 2 | * | 0 | 1 | * | 1 | 2 | * | 2 | 5 |
| | | post | 1 | 2 | 8 | * | 0 | 4 | * | 3 | 1 | * | 2 | 2 |
| 146 | 300 | pre | 0 | 0 | 0 | 0 | * | 1 | * | 0 | 7 | * | 3 | 8 |
| | | post | 0 | 0 | 4 | 5 | * | 1 | * | 4 | 5 | * | 4 | 9 |
| 147 | 300 | pre | 0 | 1 | 0 | 0 | * | 1 | * | 0 | 5 | * | 3 | 7 |
| | | post | 0 | 0 | 4 | 5 | * | 4 | * | 1 | 4 | * | 3 | 5 |
| 148 | 300 | pre | 0 | 0 | 0 | 0 | * | 0 | * | 0 | 1 | * | 0 | 2 |
| | | post | 0 | 0 | 3 | 4 | * | 2 | * | 2 | 1 | * | 1 | 3 |
| 149 | 300 | pre | 0 | 0 | 3 | 0 | * | 0 | * | 0 | 0 | * | 0 | 0 |
| | | post | 0 | 0 | 0 | 4 | * | 2 | * | 2 | 0 | * | 0 | 2 |
| 150 | 300 | pre | 2 | 4 | 4 | 2 | * | 3 | * | 4 | 8 | * | 7 | 9 |
| | | post | 2 | 4 | 6 | 5 | * | 4 | * | 4 | 6 | * | 6 | 8 |
| 151 | 300 | pre | 0 | 0 | 0 | 2 | * | 0 | * | 0 | 4 | * | 0 | 0 |
| | | post | 0 | 1 | 4 | 5 | * | 3 | * | 3 | 2 | * | 2 | 4 |
| 152 | 300 | pre | 3 | 4 | 5 | 4 | * | 3 | * | 4 | 8 | * | 7 | 7 |
| | | post | 2 | 4 | 6 | 6 | * | 5 | * | 5 | 8 | * | 6 | 9 |
| 153 | 300 | pre | 1 | 3 | 3 | 0 | * | 1 | * | 3 | 8 | * | 7 | 7 |
| | | post | 4 | 4 | 5 | 6 | * | 4 | * | 4 | 6 | * | 5 | 8 |
| 154 | 300 | pre | 4 | 5 | 4 | 2 | * | 2 | * | 4 | 8 | * | 8 | 9 |
| | | post | 5 | 6 | * | * | * | 5 | * | 7 | * | * | * | * |
| 155 | 300 | pre | 3 | 4 | 4 | 1 | * | 1 | * | 3 | 8 | * | 8 | 9 |
| | | post | 1 | 5 | 6 | 6 | * | 5 | * | 6 | 6 | * | 7 | 8 |
| 156 | 300 | pre | 2 | 2 | 0 | 0 | * | * | * | 0 | 6 | * | 4 | 9 |
| | | post | 0 | 1 | 4 | 5 | * | 4 | * | 4 | 5 | * | 4 | 9 |
| 157 | 300 | pre | 1 | 3 | 2 | 1 | * | 5 | * | 5 | 5 | * | 6 | 8 |
| | | post | 4 | 4 | 6 | 5 | * | 5 | * | 5 | 5 | * | 6 | 7 |
| 158 | 300 | pre | 3 | 4 | 3 | 2 | * | 3 | * | 5 | 8 | * | 7 | 9 |
| | | post | 4 | 5 | 5 | 5 | * | 6 | * | 5 | 5 | * | 6 | 7 |
| 159 | 300 | pre | 0 | 0 | 0 | 0 | * | 0 | * | 0 | 3 | * | 0 | 9 |
| | | post | 2 | 2 | 5 | 4 | * | 3 | * | 3 | 3 | * | 3 | 3 |

-continued

| | dose g/ha | appl. time | | | | | | | | | | | | |
|---|---|---|---|---|---|---|---|---|---|---|---|---|---|---|
| 160 | 300 | pre | 0 | 0 | 1 | 0 | * | 0 | * | 2 | 2 | * | 0 | 8 |
| | | post | 0 | 1 | 4 | 3 | * | 2 | * | 2 | 3 | * | 2 | 4 |
| 161 | 300 | pre | 0 | 0 | 0 | * | 0 | 1 | * | 0 | 0 | * | 0 | 0 |
| | | post | 0 | 1 | 3 | * | 0 | 2 | * | 0 | 0 | * | 0 | 1 |
| 162 | 300 | pre | 0 | 0 | 0 | * | 0 | 0 | * | 0 | 0 | * | 0 | 0 |
| | | post | 0 | 0 | 3 | * | 0 | 2 | * | 0 | 0 | * | 0 | 0 |
| 163 | 300 | pre | 0 | 0 | 0 | * | 0 | 0 | * | 0 | 0 | * | 0 | 3 |
| | | post | 1 | 1 | 5 | * | 0 | 4 | * | 2 | 0 | * | 0 | 2 |
| 164 | 300 | pre | 0 | 0 | 0 | * | 2 | 0 | * | 0 | 0 | * | 0 | 5 |
| | | post | 0 | 1 | 6 | * | 0 | 4 | * | 3 | 1 | * | 1 | 1 |
| 165 | 300 | pre | 0 | 3 | 5 | * | 2 | 2 | * | 2 | 8 | * | 8 | 9 |
| | | post | 2 | 3 | 9 | * | 0 | 6 | * | 3 | 3 | * | 2 | 5 |
| 166 | 300 | pre | 0 | 1 | 4 | * | 2 | 1 | * | 1 | 5 | * | 7 | 5 |
| | | post | 1 | 2 | 5 | * | 2 | 7 | * | 2 | 3 | * | 3 | 4 |
| 167 | 300 | pre | 2 | 3 | 5 | * | 4 | 2 | * | 3 | 8 | * | 8 | 9 |
| | | post | 2 | 3 | 6 | * | 5 | 6 | * | 3 | 6 | * | 6 | 8 |
| 168 | 300 | pre | 2 | 3 | 4 | * | 0 | 3 | * | 1 | 7 | * | 5 | 8 |
| | | post | 2 | 3 | 8 | * | 2 | 7 | * | 2 | 4 | * | 4 | 5 |
| 169 | 300 | pre | 3 | 3 | 5 | * | 5 | 2 | * | 3 | 8 | * | 6 | 9 |
| | | post | 3 | 3 | 9 | * | 5 | 6 | * | 3 | 5 | * | 5 | 6 |
| 170 | 300 | pre | 0 | 0 | 0 | * | 0 | 0 | * | 0 | 0 | * | 0 | 2 |
| | | post | 0 | 1 | 4 | * | 0 | 5 | * | 1 | 0 | * | 0 | 0 |
| 171 | 300 | pre | 0 | 0 | 1 | * | 0 | 0 | * | 0 | 3 | * | 2 | 6 |
| | | post | 1 | 2 | 4 | * | 0 | 4 | * | 1 | 2 | * | 2 | 3 |
| 172 | 300 | pre | 0 | 0 | 0 | * | * | 0 | * | 0 | 0 | * | 0 | 0 |
| | | post | 1 | 1 | 2 | * | * | 2 | * | 1 | 1 | * | 2 | 2 |
| 173 | 300 | pre | 1 | 3 | 6 | * | * | 2 | * | 2 | 8 | * | 8 | 9 |
| | | post | 2 | 3 | 6 | * | * | 7 | * | 3 | 6 | * | 6 | 7 |
| 174 | 300 | pre | 3 | 3 | 5 | * | 0 | 3 | * | 2 | 8 | * | 5 | 8 |
| | | post | 2 | 3 | 6 | * | 4 | 7 | * | 3 | 5 | * | 5 | 5 |
| 175 | 300 | pre | 0 | 0 | 2 | * | 0 | 1 | * | 0 | 4 | * | 1 | 7 |
| | | post | 1 | 1 | 6 | * | 1 | 7 | * | 1 | 5 | * | 5 | 5 |
| 176 | 400 | pre | 3 | 2 | * | * | 2 | 3 | * | 2 | 7 | * | * | 8 |
| | | post | 3 | 4 | * | * | 2 | 2 | * | 2 | 4 | * | * | 6 |
| 177 | 400 | pre | 7 | 5 | * | * | 5 | 4 | * | 4 | 8 | * | * | 9 |
| | | post | 3 | 5 | * | * | 4 | 6 | * | 4 | 6 | * | * | 7 |
| 178 | 400 | pre | 2 | 2 | * | * | 2 | 1 | * | 1 | 6 | * | * | 8 |
| | | post | 1 | 3 | * | * | 4 | 4 | * | 3 | 3 | * | * | 4 |
| 188 | 400 | pre | 4 | 5 | * | * | 6 | 4 | * | 5 | 9 | * | * | 9 |
| | | post | 3 | 4 | * | * | 3 | 5 | * | 3 | 7 | * | * | 8 |
| 190 | 400 | pre | 5 | 6 | * | * | 5 | 5 | * | 5 | 9 | * | * | 9 |
| | | post | 4 | 5 | * | * | 4 | 7 | * | 3 | 8 | * | * | 9 |
| 191 | 400 | pre | 4 | 4 | * | * | 5 | 5 | * | 4 | 9 | * | * | 9 |
| | | post | 4 | 4 | * | * | 4 | 7 | * | 3 | 8 | * | * | 8 |
| 192 | 400 | pre | 4 | 4 | * | * | 3 | 5 | * | 4 | 8 | * | * | 9 |
| | | post | 3 | 4 | * | * | 3 | 6 | * | 2 | 7 | * | * | 8 |
| 193 | 400 | pre | 4 | 5 | * | * | 3 | 4 | * | 4 | 8 | * | * | 9 |
| | | post | 4 | 4 | * | * | 4 | 5 | * | 3 | 8 | * | * | 9 |

| Ex. No. | dose g/ha | appl. time | GALAP | STEME | CHEAL | VERPE | LAMPU | VIOAR | SIDSP | AMBAR | ABUTH | IPOPU | SINAL | AMARE |
|---|---|---|---|---|---|---|---|---|---|---|---|---|---|---|
| 13 | 100 | pre | * | * | * | * | * | * | * | * | * | * | 5 | * |
| | 0 | post | * | * | * | * | * | * | * | * | * | * | 8 | * |
| 14 | 100 | pre | * | * | * | * | * | * | * | * | * | * | 8 | * |
| | 0 | post | * | * | * | * | * | * | * | * | * | * | 8 | * |
| 15 | 100 | pre | * | * | * | * | * | * | * | * | * | * | 6 | * |
| | 0 | post | * | * | * | * | * | * | * | * | * | * | 6 | * |
| 16 | 100 | pre | * | * | * | * | * | * | * | * | * | * | 2 | * |
| | 0 | post | * | * | * | * | * | * | * | * | * | * | 5 | * |
| 24 | 300 | pre | 0 | 0 | * | 0 | * | 0 | * | * | * | 0 | * | * |
| | | post | 0 | 0 | * | 0 | * | 0 | * | * | * | 0 | * | * |
| 25 | 300 | pre | 0 | 0 | * | 0 | * | 0 | * | * | * | 0 | * | * |
| | | post | 0 | 0 | * | 1 | * | 1 | * | * | * | 1 | * | * |
| 26 | 300 | pre | 2 | 0 | 0 | 0 | * | * | * | * | 0 | 0 | * | 0 |
| | | post | 2 | 4 | 0 | 4 | * | * | * | * | 4 | 1 | * | 5 |
| 27 | 300 | pre | 0 | 0 | 0 | 0 | * | * | * | * | 0 | 0 | * | 0 |
| | | post | 1 | 2 | 0 | 3 | * | * | * | * | 3 | 2 | * | 4 |
| 28 | 300 | pre | 2 | 7 | * | 9 | 8 | 8 | 4 | 4 | 4 | 2 | * | 9 |
| | | post | 5 | 4 | * | 6 | * | 6 | 6 | 5 | 4 | 4 | * | 6 |
| 29 | 300 | pre | 0 | 7 | 8 | 8 | * | * | * | * | 0 | 0 | * | 9 |
| | | post | 3 | 5 | 6 | 8 | * | * | * | * | 5 | 4 | * | 7 |
| 30 | 300 | pre | 6 | 9 | * | 9 | 9 | 8 | 8 | 8 | 6 | 6 | * | 9 |
| | | post | 5 | 6 | * | 6 | * | 7 | 8 | 5 | 6 | 6 | * | 5 |
| 31 | 300 | pre | 7 | 9 | * | 9 | 9 | 8 | * | * | 8 | 5 | * | 9 |
| | | post | 6 | 7 | * | 9 | 7 | 8 | * | * | 8 | 6 | * | 7 |
| 32 | 300 | pre | 1 | 6 | * | 8 | 3 | 8 | * | * | 3 | 1 | * | 9 |
| | | post | 4 | 5 | * | 9 | 5 | 7 | * | * | 4 | 5 | * | 5 |
| 33 | 300 | pre | 0 | 0 | * | 0 | 0 | 0 | * | * | 0 | 5 | * | 0 |
| | | post | 0 | 0 | * | 0 | 0 | 0 | * | * | 0 | 1 | * | 0 |

| | | | | | | | | | | | | | |
|---|---|---|---|---|---|---|---|---|---|---|---|---|---|
| 34 | 300 | pre | 2 | 8 | * | 9 | 8 | 9 | * | 8 | 3 | 5 | * | 8 |
| | | post | 6 | 6 | * | 9 | 6 | 6 | * | 5 | 6 | 6 | * | 7 |
| 39 | 300 | pre | 2 | 9 | * | 9 | 8 | 9 | * | 3 | 3 | 3 | * | 9 |
| | | post | 5 | 5 | * | 9 | 5 | 7 | * | 3 | 3 | 5 | * | 5 |
| 109 | 300 | pre | 0 | 0 | 6 | 0 | 0 | 0 | 0 | * | 0 | 0 | * | 6 |
| | | post | 0 | 0 | 0 | 7 | 0 | 0 | 1 | * | 0 | 2 | * | 1 |
| 110 | 300 | pre | 2 | 9 | * | 9 | 9 | 9 | 9 | * | 5 | 3 | * | 9 |
| | | post | 8 | 7 | * | 9 | 7 | 8 | 6 | * | 6 | 4 | * | 6 |
| 111 | 300 | pre | 5 | 9 | 8 | 9 | 8 | * | 6 | * | 5 | 3 | * | 9 |
| | | post | 6 | 8 | 9 | 9 | 8 | * | 6 | * | 6 | 4 | * | 6 |
| 112 | 300 | pre | 8 | 9 | * | 9 | 9 | 8 | * | * | 8 | 9 | * | 9 |
| | | post | 7 | 8 | * | 9 | 8 | 9 | * | * | 8 | 7 | * | 8 |
| 113 | 300 | pre | 8 | 9 | * | 9 | 8 | 8 | * | * | 9 | 9 | * | 9 |
| | | post | 7 | 8 | * | 9 | 8 | 8 | * | * | 8 | 8 | * | 7 |
| 114 | 300 | pre | 8 | 9 | * | 9 | 8 | 8 | * | * | 9 | 9 | * | 9 |
| | | post | 7 | 8 | * | 9 | 8 | 8 | * | * | 8 | 8 | * | 7 |
| 115 | 300 | pre | 8 | 9 | * | 9 | 9 | 8 | * | * | 9 | 9 | * | 9 |
| | | post | 7 | 8 | * | 8 | 8 | 8 | * | * | 8 | 8 | * | 8 |
| 116 | 300 | pre | 0 | 6 | * | 9 | 8 | 7 | * | * | 2 | 4 | * | 8 |
| | | post | 3 | 4 | * | 9 | 7 | 5 | * | * | 4 | 5 | * | 5 |
| 117 | 300 | pre | 1 | 5 | * | 9 | 6 | 8 | * | * | 4 | 4 | * | 9 |
| | | post | 4 | 4 | * | 9 | 5 | 7 | * | * | 4 | 5 | * | 7 |
| 118 | 300 | pre | 1 | 2 | * | 8 | 3 | 7 | * | * | 1 | 2 | * | 9 |
| | | post | 3 | 3 | * | 9 | 4 | 5 | * | * | 2 | 4 | * | 5 |
| 119 | 300 | pre | 0 | 0 | * | 0 | 0 | 2 | * | * | 0 | 0 | * | 0 |
| | | post | 2 | 2 | * | 3 | 1 | 5 | * | * | 1 | 3 | * | 4 |
| 120 | 300 | pre | 6 | 9 | * | 8 | 8 | 8 | * | * | 5 | 5 | * | 9 |
| | | post | 6 | 4 | * | 9 | 8 | 7 | * | * | 5 | 4 | * | 5 |
| 121 | 300 | pre | 3 | 8 | * | 9 | 7 | 8 | * | * | 5 | 4 | * | 9 |
| | | post | 6 | 5 | * | 9 | 7 | 8 | * | * | 4 | 5 | * | 6 |
| 122 | 300 | pre | * | * | * | * | * | * | * | * | * | * | * | * |
| | | post | * | * | * | * | * | * | * | * | * | * | * | * |
| 123 | 300 | pre | 0 | 0 | * | 2 | 2 | 4 | * | * | 0 | 0 | * | 4 |
| | | post | 3 | 4 | * | 5 | 3 | 5 | * | * | 2 | 6 | * | 4 |
| 124 | 300 | pre | 3 | 9 | * | 9 | 8 | 9 | * | * | 7 | 9 | * | 9 |
| | | post | 4 | 5 | * | 9 | 6 | 8 | * | * | 6 | 7 | * | 6 |
| 125 | 300 | pre | 4 | 9 | * | 9 | 9 | 9 | * | * | 9 | 7 | * | 9 |
| | | post | 5 | 6 | * | 9 | 6 | 8 | * | * | 5 | 7 | * | 6 |
| 126 | 300 | pre | 1 | 7 | * | 8 | 4 | 8 | * | * | 2 | 3 | * | 9 |
| | | post | 4 | 4 | * | 9 | 5 | 8 | * | * | 4 | 6 | * | 5 |
| 127 | 300 | pre | 0 | 7 | * | 7 | 3 | 8 | * | * | 2 | 4 | * | 8 |
| | | post | 3 | 5 | * | 6 | 4 | 8 | * | * | 4 | 6 | * | 6 |
| 128 | 300 | pre | 5 | 9 | * | 9 | 9 | 9 | * | * | 9 | 9 | * | 9 |
| | | post | 6 | 6 | * | 9 | 6 | 8 | * | * | 6 | 8 | * | 7 |
| 129 | 300 | pre | 5 | 9 | * | 9 | 9 | 9 | * | * | 9 | 9 | * | 9 |
| | | post | 5 | 5 | * | 9 | 6 | 8 | * | * | 6 | 9 | * | 6 |
| 130 | 300 | pre | 4 | 9 | * | 9 | 6 | 9 | * | * | 7 | 6 | * | 8 |
| | | post | 5 | 6 | * | 8 | 6 | 8 | * | * | 5 | 9 | * | 6 |
| 131 | 300 | pre | 0 | 4 | * | 7 | 0 | 8 | * | * | 0 | 5 | * | 8 |
| | | post | 4 | 4 | * | 7 | 4 | 7 | * | * | 4 | 5 | * | 4 |
| 132 | 300 | pre | 0 | 0 | * | 0 | 0 | 3 | * | * | 0 | 3 | * | 5 |
| | | post | 3 | 3 | * | 4 | 3 | 5 | * | * | 2 | 5 | * | 5 |
| 133 | 400 | pre | 7 | * | * | 9 | 9 | * | * | * | 9 | 9 | * | * |
| | | post | 9 | * | * | 8 | 8 | * | * | * | 9 | 9 | * | * |
| 134 | 400 | pre | 3 | * | * | 9 | 7 | * | * | * | 6 | 4 | * | * |
| | | post | 7 | * | * | 9 | 8 | * | * | * | 9 | 9 | * | * |
| 135 | 300 | pre | 3 | 8 | * | 9 | 8 | * | * | * | 8 | 9 | * | * |
| | | post | 6 | 7 | 8 | 9 | 9 | * | * | * | 7 | 9 | * | * |
| 136 | 300 | pre | 1 | 9 | * | 9 | 8 | * | * | * | 6 | 9 | * | * |
| | | post | 6 | 8 | 6 | 9 | 7 | * | * | * | 8 | 8 | * | * |
| 137 | 300 | pre | 0 | 0 | 5 | 0 | 0 | * | * | * | 0 | 0 | * | * |
| | | post | 1 | 1 | * | 2 | 2 | * | * | * | 1 | 2 | * | * |
| 138 | 300 | pre | 4 | 9 | * | 9 | 9 | * | * | * | 7 | 9 | * | * |
| | | post | 5 | 7 | 7 | 9 | 8 | * | * | * | 7 | 8 | * | * |
| 139 | 300 | pre | 0 | 0 | * | 0 | 0 | * | * | * | 0 | 0 | * | * |
| | | post | 1 | 1 | 4 | 3 | 2 | * | * | * | 2 | 4 | * | * |
| 140 | 300 | pre | 4 | 9 | * | 9 | 9 | 9 | * | 8 | 4 | 6 | * | 8 |
| | | post | 7 | 6 | * | 9 | 8 | 6 | * | 6 | 8 | 9 | * | 9 |
| 141 | 300 | pre | 1 | 9 | * | 9 | 8 | 8 | * | 5 | 2 | 4 | * | 5 |
| | | post | 5 | 5 | * | 8 | 7 | 6 | * | 6 | 5 | 9 | * | 9 |
| 142 | 300 | pre | 1 | 4 | * | 5 | 1 | 7 | * | 0 | 0 | 1 | * | 0 |
| | | post | 2 | 3 | * | 5 | 4 | 6 | * | 5 | 3 | 5 | * | 5 |
| 143 | 300 | pre | 3 | 9 | * | 9 | 8 | 9 | * | 8 | 4 | 5 | * | 8 |
| | | post | 6 | 5 | * | 8 | 5 | 6 | * | 7 | 6 | 7 | * | 8 |
| 144 | 300 | pre | 0 | * | * | 4 | 4 | 4 | * | 0 | 0 | 4 | * | 3 |
| | | post | 4 | * | * | 6 | 3 | 5 | * | 5 | 3 | 4 | * | 6 |
| 145 | 300 | pre | 0 | 3 | * | 6 | 3 | 6 | * | 2 | 0 | 2 | * | 5 |
| | | post | 5 | 5 | * | 7 | 5 | 6 | * | 6 | 5 | 5 | * | 8 |
| 146 | 300 | pre | 0 | 8 | * | 9 | 4 | 8 | * | 4 | 3 | 1 | * | 9 |
| | | post | 4 | 6 | * | 7 | 4 | 7 | * | 4 | 3 | 4 | * | 4 |

-continued

| | | | | | | | | | | | | | |
|---|---|---|---|---|---|---|---|---|---|---|---|---|---|
| 147 | 300 | pre | 0 | 6 | * | 9 | 3 | 7 | * | 3 | 3 | 3 | * | 9 |
| | | post | 4 | 5 | * | 6 | 4 | 5 | * | 4 | 4 | 5 | * | 4 |
| 148 | 300 | pre | 0 | 0 | * | 8 | 0 | 8 | * | 0 | 1 | 0 | * | 9 |
| | | post | 4 | 3 | * | 4 | 3 | 6 | * | 3 | 2 | 4 | * | 4 |
| 149 | 300 | pre | 0 | 0 | * | 2 | 1 | 5 | * | 0 | 0 | 0 | * | 8 |
| | | post | 4 | 3 | * | 5 | 4 | 4 | * | 4 | 1 | 4 | | 4 |
| 150 | 300 | pre | 2 | 9 | * | 9 | 9 | 9 | * | 7 | 4 | 6 | * | 9 |
| | | post | 5 | 5 | * | 7 | 7 | 7 | * | 6 | 6 | 6 | | 7 |
| 151 | 300 | pre | 0 | 6 | * | 8 | 2 | 9 | * | 4 | 1 | 1 | * | 9 |
| | | post | 4 | 5 | * | 6 | 4 | 7 | * | 4 | 2 | 4 | * | 6 |
| 152 | 300 | pre | 4 | 9 | * | 9 | 8 | 9 | * | 8 | 7 | 9 | * | 8 |
| | | post | 7 | 7 | * | 7 | 7 | 7 | * | 7 | 6 | 5 | * | 7 |
| 153 | 300 | pre | 1 | 9 | * | 9 | 8 | 9 | * | 4 | 5 | 5 | * | 9 |
| | | post | 5 | 6 | * | 8 | 5 | 6 | * | 4 | 5 | 5 | * | 5 |
| 154 | 300 | pre | 3 | 9 | * | 9 | 9 | 9 | * | 8 | 7 | 7 | * | 9 |
| | | post | * | * | * | * | * | * | * | * | * | * | * | * |
| 155 | 300 | pre | 4 | 9 | * | 9 | 8 | 9 | * | 8 | 8 | 6 | * | 9 |
| | | post | 6 | 7 | * | 7 | 5 | 7 | * | 5 | 6 | 5 | * | 5 |
| 156 | 300 | pre | 0 | 8 | * | 9 | 4 | 9 | * | 4 | 4 | 3 | * | 9 |
| | | post | 5 | 7 | * | 7 | 4 | 6 | * | 4 | 4 | 4 | * | 5 |
| 157 | 300 | pre | 3 | 9 | * | 9 | 8 | 9 | * | 7 | 7 | 9 | * | 9 |
| | | post | 4 | 5 | * | 9 | 6 | 8 | * | 5 | 6 | 7 | * | 6 |
| 158 | 300 | pre | 4 | 9 | * | 9 | 9 | 9 | * | 7 | 9 | 7 | * | 9 |
| | | post | 5 | 6 | * | 9 | 6 | 8 | * | 5 | 5 | 7 | * | 6 |
| 159 | 300 | pre | 1 | 7 | * | 8 | 4 | 8 | * | 4 | 2 | 3 | * | 9 |
| | | post | 4 | 4 | * | 9 | 5 | 8 | * | 4 | 4 | 6 | * | 5 |
| 160 | 300 | pre | 0 | 7 | * | 7 | 3 | 8 | * | 2 | 2 | 4 | * | 2 |
| | | post | 3 | 5 | * | 6 | 4 | 2 | * | 5 | 4 | 6 | * | 6 |
| 161 | 300 | pre | 0 | 0 | * | 1 | 0 | 0 | * | 0 | 0 | 0 | * | 0 |
| | | post | 0 | 1 | * | 1 | 1 | 5 | * | 1 | 1 | 3 | * | 2 |
| 162 | 300 | pre | 0 | 0 | * | 0 | 0 | 0 | * | 0 | 0 | 0 | * | 0 |
| | | post | 1 | 1 | * | 1 | 5 | 5 | * | 0 | 0 | 2 | * | 0 |
| 163 | 300 | pre | 1 | 0 | * | 3 | 0 | 2 | * | 0 | 0 | 2 | * | 0 |
| | | post | 2 | 3 | * | 6 | 4 | 5 | * | 3 | 2 | 4 | * | 5 |
| 164 | 300 | pre | 0 | 6 | * | 4 | 1 | 7 | * | 1 | 0 | 1 | * | 3 |
| | | post | 2 | 4 | * | 6 | 5 | 6 | * | 3 | 3 | 5 | * | 8 |
| 165 | 300 | pre | 4 | 9 | * | 9 | 9 | 9 | * | 8 | 4 | 6 | * | 8 |
| | | post | 8 | 6 | * | 9 | 7 | 6 | * | 6 | 7 | 9 | * | 8 |
| 166 | 300 | pre | 2 | 5 | * | 8 | 7 | 8 | * | 6 | 2 | 4 | * | 8 |
| | | post | 6 | 5 | * | 8 | 5 | 7 | * | 4 | 6 | 5 | * | 8 |
| 167 | 300 | pre | 2 | 8 | * | 9 | 8 | 8 | * | 8 | 4 | 9 | * | 8 |
| | | post | 5 | 7 | * | 8 | 6 | 6 | * | 4 | 6 | 5 | * | 8 |
| 168 | 300 | pre | 1 | 5 | * | 9 | 6 | 9 | * | 5 | 4 | 3 | * | 9 |
| | | post | 5 | 5 | * | 9 | 8 | 8 | * | 6 | 5 | 8 | * | 7 |
| 169 | 300 | pre | 1 | 9 | * | 9 | 8 | 9 | * | 5 | 4 | 6 | * | 9 |
| | | post | 5 | 4 | * | 8 | 7 | 7 | * | 5 | 6 | 6 | * | 7 |
| 170 | 300 | pre | 0 | 0 | * | 0 | 1 | 5 | * | 0 | 0 | 2 | * | 6 |
| | | post | 2 | 1 | * | 3 | 3 | 5 | * | 3 | 2 | 4 | * | 5 |
| 171 | 300 | pre | 0 | 0 | * | 3 | 2 | 8 | * | 0 | 0 | 1 | * | 7 |
| | | post | 4 | 2 | * | 5 | 5 | 7 | * | 4 | 4 | 4 | * | 5 |
| 172 | 300 | pre | 0 | 0 | * | 2 | 2 | 4 | * | 1 | 0 | 0 | * | 4 |
| | | post | 3 | 4 | * | 5 | 3 | 5 | * | 2 | 2 | 6 | * | 4 |
| 173 | 300 | pre | 6 | 8 | * | 9 | 9 | 9 | * | 8 | 5 | 8 | * | 8 |
| | | post | 6 | 7 | * | 9 | 6 | 7 | * | 6 | 6 | 8 | * | 8 |
| 174 | 300 | pre | 4 | 8 | * | 9 | 8 | 9 | * | 6 | 4 | 6 | * | 9 |
| | | post | 5 | 4 | * | 9 | 7 | 8 | * | 6 | 5 | 8 | * | 7 |
| 175 | 300 | pre | 0 | 2 | * | 7 | 4 | 8 | * | 1 | 0 | 0 | * | 8 |
| | | post | 5 | 4 | * | 9 | 7 | 8 | * | 6 | 5 | 8 | * | 7 |
| 176 | 400 | pre | 3 | * | * | 9 | 8 | * | * | * | 2 | 8 | * | * |
| | | post | 8 | * | * | 8 | 7 | * | * | * | 8 | 9 | * | * |
| 177 | 400 | pre | 5 | * | * | 9 | * | * | * | * | 6 | 9 | * | * |
| | | post | 7 | * | * | 9 | * | * | * | * | 7 | 6 | * | * |
| 178 | 400 | pre | 4 | * | * | 8 | * | * | * | * | 2 | 3 | * | * |
| | | post | 5 | * | * | 9 | * | * | * | * | 5 | 4 | * | * |
| 188 | 400 | pre | 8 | * | * | 9 | 9 | * | * | * | 9 | 9 | * | * |
| | | post | 9 | * | * | 9 | 8 | * | * | * | 8 | 9 | * | * |
| 190 | 400 | pre | 9 | * | * | 9 | 9 | * | * | * | 9 | 9 | * | * |
| | | post | 9 | * | * | 9 | 8 | * | * | * | 9 | 9 | * | * |
| 191 | 400 | pre | 8 | * | * | 9 | 9 | * | * | * | 9 | 9 | * | * |
| | | post | 9 | * | * | 9 | 8 | * | * | * | 9 | 9 | * | * |
| 192 | 400 | pre | 7 | * | * | 9 | 8 | * | * | * | 9 | 9 | * | * |
| | | post | 9 | * | * | 9 | 8 | * | * | * | 9 | 9 | * | * |
| 193 | 400 | pre | 7 | * | * | 9 | 8 | * | * | * | 8 | 9 | * | * |
| | | post | 8 | * | * | 8 | 7 | * | * | * | 8 | 9 | * | * |

We claim:
1. A compound of the general formula I

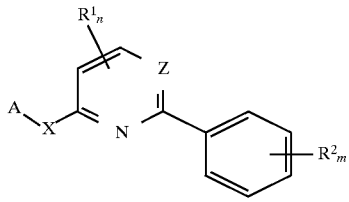

wherein
A represents a substituted aryl group or an optionally substituted pyridyl or pyrazolyl group or a difluorobenzodioxolyl group;
m represents an integer from 0 to 5;
n represents an integer from 0 to 2;
$R^1$ (or each $R^1$) independently represents a hydrogen atom, a halogen atom, an optionally substituted alkyl, alkenyl, alkynyl, alkoxy, alkoxyalkoxy, alkoxyalkyl, dialkoxyalkyl, alkylthio, amino, alkylamino, dialkylamino, alkoxyamino or formamidino group;
$R^2$ (or each $R^2$) independently represents a hydrogen atom, a halogen atom, an optionally substituted alkyl, alkenyl, alkynyl, alkoxy, alkoxyalkyl, alkoxyalkoxy, alkylthio, alkylsulphinyl, alkylsulphonyl group or a nitro, cyano, haloalkyl, haloalkoxy, haloalkylthio or $SF_5$ group,
X represents any oxygen or sulphur, atom; and
Z represents a nitrogen atom.

2. A compound as claimed in claim 1 wherein A represents a phenyl, pyridyl or pyrazolyl group being substituted by one or more of the same or different substituents selected from halogen atoms, alkyl groups, alkoxy groups, haloalkyl groups, haloalkoxy groups, haloalkylthio groups and $SF_5$ groups.

3. A compound as claimed in claim 2 wherein the substituents on A are in the meta-position relative to the point of attachment of X.

4. A compound as claimed in claim 3 wherein A is meta-substituted by a chlorine atom or a trifluoromethyl or difluoromethoxy group.

5. A compound as claimed in claim 4 wherein A is a 2-difluoromethoxypyrid-4-yl group.

6. A compound as claimed in claim 1 selected from the group consisting of:

2-(2',4'difluorophenyl)-6-methyl-4(1"-methyl-3"-trifluoromethylpyrazol-5¹¹-yloxy)pyrimidine,
2-(2',4'-difluorophenyl)-6-methyl-4-(3"-trifluoromethylphenoxy)pyrimidine,
2-(3'-chlorophenyl)-5-methyl-4-(1"-methyl-3"-trifluoromethylpyrazol-5"-yloxy)pyrimidine,
2-(3'-chlorophenyl)-5-methyl-4-(3"-trifluoromethylphenoxy)pyrimidine,
2-(4'-fluorophenyl)-6-methyl-4-(3"-trifluoromethylphenoxy)pyrimidine,
2-(4'-fluorophenyl)-4-(1"-methyl-3"-trifluoromethylpyrazol-5"-yloxy)-5-methylpyrimidine,
2-(4'-fluorophenyl)-4-(1"-methyl-3"-trifluoromethylpyrazol-5"-yloxy)-6-methyl-pyrimidine,
4-(2"-chloropyrid-4"yloxy)-2-(2',4'-difluorophenyl)-5-methylpyrimidine,
4-(2"¹-chloropyrid-4"-yloxy)-5,6-dimethyl-2-(4'-trifluoromethoxyphenyl)pyrimidine,
4-(2"-chloropyrid-4"-yloxy)-5,6-dimethyl-2-(4'-trifluoromethylphenyl)pyrimidine,
4-(2"-chloropyrid-4"-yloxy)-5-methyl-2-(4'-trifluoromethoxyphenyl)pyrimidine,
4-(2"-chloropyrid-4"-yloxy)-5-methyl-2-(4'-trifluoromethylphenyl)pyrimidine,
4-(2"-chloropyrid-4"-yloxy)-6-methyl-2-(4'-trifluoromethoxyphenyl)pyrimidine,
4-(2"-chloropyrid-4"-yloxy)-6-methyl-2-(4'-trifluoromethylphenyl)pyrimidine,
5,6-dimethyl-2-(4'-trifluoromethoxyphenyl)-4-(1"-methyl-3"-trifluoromethylpyrazol-5"-yloxy)pyrimidine,
5,6-dimethyl-2-(4'-trifluoromethoxyphenyl)-4-(3"-trifluoromethylphenoxy)pyrimidine,
5,6-dimethyl-2-(4'-trifluoromethylphenyl)-4-(3"-trifluoromethylphenoxy)pyrimidine,
5-6-dimethyl-4-(1"-methyl-3"-trifluoromethylpyrazol-5"-yloxy)-2-(4'-trifluoromethylphenyl)pyrimidine,
5-methyl-2-(3'-methylphenyl)-4-(1"-methyl-3"-trifluoromethylpyrazol-5"-yloxy)pyrimidine,
5-methyl-2-(3'-methylphenyl)-4-(3"-trifluoromethylphenoxy)pyrimidine,
5-methyl-2-(4'-trifluoromethoxyphenyl)-4-(1"-methyl-3"-trifluoromethylpyrazol-5"-yloxy)pyrimidine,
5-methyl-2-(4'-trifluoromethoxyphenyl)-4-(3"-trifluoromethylphenoxy)pyrimidine,
5-methyl-2-(4'-trifluoromethylphenyl)-4-(1"-methyl-3"-trifluoromethylpyrazol-5"-yloxy)pyrimidine,
5-methyl-4-(3"-trifluoromethylphenoxy)-2-(4'-trifluoromethylphenyl)pyrimidine,
6-methyl-2-(4'-trifluoromethoxyphenyl)-4-(1"- methyl-3"-trifluoromethylpyrazol-5"-yloxy)pyrimidine,
6-methyl-2-(4'-trifluoromethoxyphenyl)-4-(3"-trifluoromethylphenoxy)pyrimidine,
6-methyl-4-(3"-trifluoromethylphenoxy)-2-(4'-trifluoromethylphenyl)pyrimidine,
6-methyl-2-(4'-trifluoromethylphenyl)-4-(1"-methyl-3"-pentafluoroethylpyrazol-5¹¹-yloxy)pyrimidine,
6-methyl-2-(4'-cyanophenyl)-4-(1"-methyl-3"-pentafluoroethylpyrazol-5"-yloxy)pyrimidine,
6-methoxy-2-(4'-cyanophenyl)-4-(1"-methyl-3"-pentafluoroethylpyrazol-5"-yloxy)pyrimidine,
6-methyl-4-(2",2"-difluoro-1'",3'"-benzodioxol-4"-yl)-2-(4'-trifluoromethylphenyl)pyrimidine.
6-ethyl-2-(4'-trifluoromethylphenyl)-4-(1"-methylphenyl)-4-(1"-methyl-3"-trifluoromethylpyrazol-5"-yloxy)pyrimidine,
6-ethyl-2-(4'-trifluoromethylphenyl)-4-(3"-trifluoromethylphenoxy)pyrimidine,
6-methyl-2-(4'-methylsulfonylphenyl)-4-(1"-methyl-3"-pentafluoroethylpyrazol-5"-yloxy)pyrimidine,
6-ethyl-2-(4'-trifluoromethylphenyl)-4-(2'-chloropyrid-4'-yloxy)pyrimidine,
6-propargyl-2-(4'-trifluoromethylpheny)-4-(1"-methyl-3"-trifluoromethylpyrazol-5"-yloxy)pyrimidine,
6-methoxymethyl-2-(4'-chlorophenyl)-4-(1"-methyl-3"-trifluoromethylpyrazol-5"-yloxy)pyrimidine,
6-methoxymethyl-2-(4'-chlorophenyl)-4-(3"-trifluoromethylphenoxy)pyrimidine,
4-(3"-trifluoromethylphenoxy)-2-(4'-trifluromethylphenyl)pyrimidine,
4-(1"-methyl-3"-trifluoromethylpyrazol-5"-yloxy)-2-(4'-trifluoromethylphenyl)pyrimidine,
6-chloro-2-(4'-trifluoromethylphenyl)-4-(1"-methyl-3"-trifluoromethylpyrazol-5"-yloxy)pyrimidine,
6-bromo-2-(4'-trifluoromethylphenyl)-4-(1"-methyl-3"-trifluoromethylpyrazol-5"-yloxy)pyrimidine,
6-chloro-2-(4'-chloromethylphenyl)-4-(1"-methyl-3"-trifluoromethylpyrazol-5"-yloxy)pyrimidine,
6-fluoro-2-(4'-trifluoromethylphenyl)-4-(1"-methyl-3"-trifluoromethylpyrazol-5"yloxy)pyrimidine, 6-methoxy-2-(4'-trifluoromethylphenyl)-4-("3-trifluoromethylphenoxy)pyrimidine, 6-methoxy-2-(4'-trifluoromethylphenyl)-4-(1"-methyl-3"-trifluoromethylpyrazol-5"-yloxy)pyrimidine, 6-methoxy-2-(4'-trifluoromethylphenyl)-4-(2'-chloropyrid-4'-yloxy)pyrimidine, 5-methoxy-2-(4'-trifluoromethylphenyl)-4-(3"-trifluoromethylphenoxy)pyrimidine, 5-methoxy-2-(4'-trifluoromethylphenyl)-4-(1"-methyl-3"-trifluoromethylpyrazol-5"-yloxy)pyrimidine, 5-methoxy-2-(4'-trifluoromethylphenyl)-4-(2'-chloropyrid-4'-yloxy)pyrimidine, 6-ethylamino-2-(4'-trifluoromethylphenyl)-4-(1"-methyl-3"-trifluoromethylpyrazol-5"-yloxy)pyrimidine, 6-methoxyamino-2-(4'-chlorophenyl)-4-(1"-methyl-3"-trifluoromethylpyrazol-5"-yloxy)pyrimidine 6-vinyl-2-(4'-trifluoromethylphenyl)-4-(1"-methyl-3"-trifluoromethylpyrazol-5"-yloxy)pyrimidine, and 6-methyl-2-(4'-trifluoromethylphenyl)-4-(2"-difluoromethoxy-pyrid-4"-yloxy)pyrimidine.

7. A compound of general formula XV,

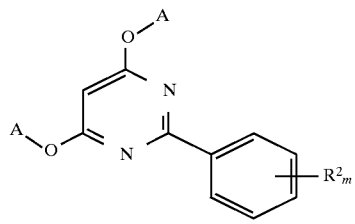

(XV)

wherein A, $R^2$ and m are defined as in claim 1.

8. A compound of formula Ia

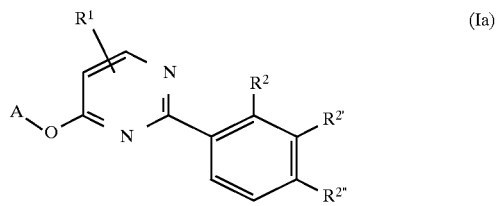

(Ia)

wherein

A represents 3-trifluoromethylphenyl, 2-chloropyrid-4-yl, 2-trifluoromethylpyrid-4-yl, 2-difluoromethoxypyrid-4-yl or 1-methyl-3-trifluoromethylpyrazol-5-yl, $R^1$ has the meaning given above; $R^2$, $R^{2'}$ and $R^{2''}$ independently represent a hydrogen atom, a fluorine, chlorine or bromine atom, one or two of them also a trifluoromethyl, trifluormethoxy or a cyano group, $R^{2''}$ can further be a $C_1$–$C_4$alkyl group, particularly tert-butyl.

* * * * *